United States Patent
Phiasivongsa et al.

(10) Patent No.: US 9,403,868 B2
(45) Date of Patent: *Aug. 2, 2016

(54) CRYSTALLINE TRIPEPTIDE EPOXY KETONE PROTEASE INHIBITORS

(71) Applicant: Onyx Therapeutics, Inc., South San Francisco, CA (US)

(72) Inventors: Pasit Phiasivongsa, Brentwood, CA (US); Louis C. Sehl, Redwood City, CA (US)

(73) Assignee: Onyx Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/639,603

(22) Filed: Mar. 5, 2015

(65) Prior Publication Data

US 2015/0175656 A1    Jun. 25, 2015

Related U.S. Application Data

(60) Continuation of application No. 14/035,644, filed on Sep. 24, 2013, now Pat. No. 9,051,353, which is a division of application No. 13/257,887, filed as application No. PCT/US2010/028126 on Mar. 22, 2010, now Pat. No. 8,604,215.

(60) Provisional application No. 61/180,561, filed on May 22, 2009, provisional application No. 61/162,196, filed on Mar. 20, 2009.

(51) Int. Cl.
| | |
|---|---|
| *A61K 31/427* | (2006.01) |
| *C07K 5/08* | (2006.01) |
| *C07D 417/12* | (2006.01) |
| *C07K 5/097* | (2006.01) |
| *C07K 1/02* | (2006.01) |

(52) U.S. Cl.
CPC ............. *C07K 5/0802* (2013.01); *A61K 31/427* (2013.01); *C07D 417/12* (2013.01); *C07K 1/026* (2013.01); *C07K 5/0821* (2013.01)

(58) Field of Classification Search
CPC .................................................. A61K 31/427
See application file for complete search history.

(56) References Cited

U.S. PATENT DOCUMENTS

| | | | |
|---|---|---|---|
| 4,733,665 A | 3/1988 | Palmaz | |
| 4,990,448 A | 2/1991 | Konishi et al. | |
| 5,071,957 A | 12/1991 | Konishi et al. | |
| 5,134,127 A | 7/1992 | Stella et al. | |
| 5,135,919 A | 8/1992 | Folkman et al. | |
| 5,340,736 A | 8/1994 | Goldberg | |
| 5,376,645 A | 12/1994 | Stella et al. | |
| 5,441,944 A | 8/1995 | Weisz et al. | |
| 5,723,492 A | 3/1998 | Chandrakumar et al. | |
| 5,756,764 A | 5/1998 | Fenteany et al. | |
| 5,831,081 A | 11/1998 | Reuscher | |
| 5,874,418 A | 2/1999 | Stella et al. | |
| 6,046,177 A | 4/2000 | Stella et al. | |
| 6,066,730 A | 5/2000 | Adams et al. | |
| 6,075,150 A | 6/2000 | Wang et al. | |
| 6,099,851 A | 8/2000 | Weisman et al. | |
| 6,133,248 A | 10/2000 | Stella | |
| 6,133,308 A | 10/2000 | Soucy et al. | |
| 6,150,415 A | 11/2000 | Hammock et al. | |
| 6,204,257 B1 | 3/2001 | Stella et al. | |
| 6,235,717 B1 | 5/2001 | Leban et al. | |
| 6,294,560 B1 | 9/2001 | Soucy et al. | |
| 6,297,217 B1 | 10/2001 | Adams et al. | |
| 6,410,512 B1 | 6/2002 | Mundy et al. | |
| 6,462,019 B1 | 10/2002 | Mundy et al. | |
| 6,492,333 B1 | 12/2002 | Mundy | |
| 6,548,668 B2 | 4/2003 | Adams et al. | |
| 6,613,541 B1 | 9/2003 | Vaddi et al. | |
| 6,617,309 B2 | 9/2003 | Tung et al. | |
| 6,656,904 B2 | 12/2003 | Mundy et al. | |
| 6,660,268 B1 | 12/2003 | Palombella et al. | |
| 6,699,835 B2 | 3/2004 | Plamondon et al. | |
| 6,740,674 B2 | 5/2004 | Klimko et al. | |
| 6,781,000 B1 | 8/2004 | Wang et al. | |
| 6,794,516 B2 | 9/2004 | Soucy et al. | |
| 6,831,099 B1 | 12/2004 | Crews et al. | |
| 6,838,252 B2 | 1/2005 | Mundy et al. | |
| 6,838,436 B1 | 1/2005 | Mundy et al. | |
| 6,849,743 B2 | 2/2005 | Soucy et al. | |
| 6,884,769 B1 | 4/2005 | Mundy et al. | |

(Continued)

FOREIGN PATENT DOCUMENTS

| | | |
|---|---|---|
| EP | 0 411 660 A1 | 2/1991 |
| EP | 1 136 498 A1 | 9/2001 |
| WO | WO-91/13904 A1 | 9/1991 |
| WO | WO-94/15956 A1 | 7/1994 |
| WO | WO-95/23797 A1 | 9/1995 |
| WO | WO-95/24914 A1 | 9/1995 |
| WO | WO-96/13266 A1 | 5/1996 |
| WO | WO-96/32105 A1 | 10/1996 |
| WO | WO-98/10779 A1 | 3/1998 |
| WO | WO-00/02548 A2 | 1/2000 |

(Continued)

OTHER PUBLICATIONS

"Definition of Cancer," [Retrieved from] http://www.medterms.com, 1 page [retrieved on Sep. 16, 2005].

Acharyya et al., Cancer cachexia is regulated by selective targeting of skeletal muscle gene products. *JCI* 114: 370-8 (2004).

Adams et al., Proteasome inhibitors: A novel class of potent and effective antitumor agents. *Cancer Res.* 59:2615-22 (1999).

Adams, Cancer Drug Discovery and Development, Protease Inhibitors in Cancer Therapy, Human Press, Chapter 20, Phase I trials, pp. 271-282 (2004).

(Continued)

*Primary Examiner* — Michael Barker
*Assistant Examiner* — Karen Cheng
(74) *Attorney, Agent, or Firm* — Marshall, Gerstein & Borun LLP

(57) ABSTRACT

The invention relates to crystalline tripeptide keto epoxide compounds, methods of their preparation, and related pharmaceutical compositions.

11 Claims, 7 Drawing Sheets

(56) References Cited

U.S. PATENT DOCUMENTS

| | | |
|---|---|---|
| 6,902,721 B1 | 6/2005 | Mundy et al. |
| 7,109,323 B2 | 9/2006 | Plamondon et al. |
| 7,189,740 B2 | 3/2007 | Zeldis |
| 7,232,818 B2 | 6/2007 | Smyth et al. |
| 7,388,017 B2 | 6/2008 | Tung et al. |
| 7,417,042 B2 | 8/2008 | Smyth et al. |
| 7,442,830 B1 | 10/2008 | Olhava et al. |
| 7,491,704 B2 | 2/2009 | Smyth et al. |
| 7,531,526 B2 | 5/2009 | Adams et al. |
| 7,687,456 B2 | 3/2010 | Zhou et al. |
| 7,691,852 B2 | 4/2010 | Shenk et al. |
| 7,700,588 B2 | 4/2010 | Merkus |
| 7,737,112 B2 | 6/2010 | Lewis et al. |
| 7,863,297 B2 | 1/2011 | Zeldis |
| 7,968,569 B2 | 6/2011 | Zeldis |
| 8,080,545 B2 | 12/2011 | Shenk et al. |
| 8,080,576 B2 | 12/2011 | Shenk et al. |
| 8,088,741 B2 | 1/2012 | Smyth et al. |
| 8,129,346 B2 | 3/2012 | Smyth et al. |
| 8,198,262 B2 | 6/2012 | Zeldis |
| 8,198,270 B2 | 6/2012 | Smyth et al. |
| 8,198,306 B2 | 6/2012 | Zeldis |
| 8,207,124 B2 | 6/2012 | Smyth et al. |
| 8,207,125 B2 | 6/2012 | Smyth et al. |
| 8,207,126 B2 | 6/2012 | Smyth et al. |
| 8,207,127 B2 | 6/2012 | Smyth et al. |
| 8,207,297 B2 | 6/2012 | Smyth et al. |
| 8,324,174 B2 | 12/2012 | Smyth et al. |
| 8,357,683 B2 | 1/2013 | Shenk et al. |
| 8,367,617 B2 | 2/2013 | Phiasivongsa et al. |
| 8,431,571 B2 | 4/2013 | Shenk et al. |
| 2002/0103127 A1 | 8/2002 | Mundy et al. |
| 2002/0107203 A1 | 8/2002 | Mundy et al. |
| 2002/0111292 A1 | 8/2002 | Mundy et al. |
| 2003/0224469 A1 | 12/2003 | Buchholz et al. |
| 2003/0236223 A1 | 12/2003 | Wagner et al. |
| 2004/0097420 A1 | 5/2004 | Palombella et al. |
| 2004/0106539 A1 | 6/2004 | Schubert et al. |
| 2004/0116329 A1 | 6/2004 | Epstein |
| 2004/0138153 A1 | 7/2004 | Ramesh et al. |
| 2004/0167139 A1 | 8/2004 | Potter |
| 2004/0171556 A1 | 9/2004 | Purandare et al. |
| 2004/0254118 A1 | 12/2004 | He et al. |
| 2004/0266664 A1 | 12/2004 | Crews et al. |
| 2005/0025734 A1 | 2/2005 | Garrett et al. |
| 2005/0101781 A1 | 5/2005 | Agoulnik et al. |
| 2005/0245435 A1 | 11/2005 | Smyth et al. |
| 2005/0256324 A1 | 11/2005 | Laidig et al. |
| 2006/0030533 A1 | 2/2006 | Smyth et al. |
| 2006/0088471 A1 | 4/2006 | Bennett et al. |
| 2006/0128611 A1 | 6/2006 | Lewis et al. |
| 2006/0241056 A1 | 10/2006 | Orlowski et al. |
| 2007/0105786 A1 | 5/2007 | Zhou et al. |
| 2007/0207950 A1 | 9/2007 | Yao et al. |
| 2007/0212756 A1 | 9/2007 | Greene et al. |
| 2008/0090785 A1 | 4/2008 | Smyth et al. |
| 2009/0099132 A1 | 4/2009 | Olhava et al. |
| 2009/0105156 A1 | 4/2009 | Phiasivongsa et al. |
| 2009/0131421 A1 | 5/2009 | Smyth et al. |
| 2009/0156473 A1 | 6/2009 | Schubert |
| 2009/0182149 A1 | 7/2009 | Kawahara et al. |
| 2009/0203698 A1 | 8/2009 | Zhou et al. |
| 2009/0215093 A1 | 8/2009 | Bennett et al. |
| 2010/0144506 A1 | 6/2010 | Shenk et al. |
| 2010/0240903 A1 | 9/2010 | Phiasivongsa et al. |
| 2011/0236428 A1 | 9/2011 | Kirk et al. |
| 2012/0077855 A1 | 3/2012 | Phiasivongsa et al. |
| 2012/0088762 A1 | 4/2012 | Shenk et al. |
| 2012/0088903 A1 | 4/2012 | Phiasivongsa et al. |
| 2012/0101025 A1 | 4/2012 | Smyth et al. |
| 2012/0101026 A1 | 4/2012 | Smyth et al. |
| 2012/0277146 A1 | 11/2012 | Smyth et al. |
| 2012/0329705 A1 | 12/2012 | Smyth et al. |
| 2013/0035295 A1 | 2/2013 | Kirk et al. |
| 2013/0041008 A1 | 2/2013 | Shenk et al. |
| 2013/0053303 A1 | 2/2013 | Shenk et al. |
| 2013/0065827 A1 | 3/2013 | Phiasivongsa |
| 2013/0072422 A1 | 3/2013 | Shenk et al. |
| 2013/0130968 A1 | 5/2013 | Zhou et al. |
| 2013/0150289 A1 | 6/2013 | Phiasivongsa et al. |
| 2013/0150290 A1 | 6/2013 | Phiasivongsa et al. |

FOREIGN PATENT DOCUMENTS

| | | |
|---|---|---|
| WO | WO-00/61167 A2 | 10/2000 |
| WO | WO-01/28579 A2 | 4/2001 |
| WO | WO-03/059898 A2 | 7/2003 |
| WO | WO-2004/089341 A1 | 10/2004 |
| WO | WO-2005/065649 A1 | 7/2005 |
| WO | WO-2005/105827 A2 | 11/2005 |
| WO | WO-2005/111008 A2 | 11/2005 |
| WO | WO-2005/111009 A2 | 11/2005 |
| WO | WO-2006/017842 A1 | 2/2006 |
| WO | WO-2006/045066 A2 | 4/2006 |
| WO | WO-2006/063154 A1 | 6/2006 |
| WO | WO-2006/086600 A1 | 8/2006 |
| WO | WO-2006/099261 A2 | 9/2006 |
| WO | WO-2006/113470 A2 | 10/2006 |
| WO | WO-2007/021666 A2 | 2/2007 |
| WO | WO-2007/056464 A1 | 5/2007 |
| WO | WO-2007/067976 A2 | 6/2007 |
| WO | WO-2007/149512 A2 | 12/2007 |
| WO | WO-2008/033807 A2 | 3/2008 |
| WO | WO-2008/091620 A2 | 7/2008 |
| WO | WO-2008/140782 A2 | 11/2008 |
| WO | WO-2009/020448 A1 | 2/2009 |
| WO | WO-2009/045497 A1 | 4/2009 |
| WO | WO-2009/051581 A1 | 4/2009 |
| WO | WO-2009/067453 A1 | 5/2009 |
| WO | WO-2009/154737 A1 | 12/2009 |
| WO | WO-2010/036357 A1 | 4/2010 |
| WO | WO-2010/048298 A1 | 4/2010 |
| WO | WO-2010/108172 A1 | 9/2010 |
| WO | WO-2010/145376 A1 | 12/2010 |
| WO | WO-2011/060179 A1 | 5/2011 |
| WO | WO-2011/109355 A1 | 9/2011 |
| WO | WO-2011/123502 A1 | 10/2011 |
| WO | WO-2011/136905 A2 | 11/2011 |

OTHER PUBLICATIONS

Adams, The development of proteasome inhibitors as anticancer drugs. *Cancer Cell*, 5: 417-21 (2003).

Almond et al., The proteasome: a novel target for cancer chemotherapy. *Leukemia*, 16(4): 433-43 (2002).

Altun et al., Effects of PS-341 on the activity and composition of proteasomes in multiple myeloma cells. *Cancer Res*. 65:7896 (2005).

Alves et al., Diels-alder reactions of alkyl 2H-azirine-3-carboxylates with furans. *J. Chem. Soc. Perkin Trans*. 1: 2969-6 (2001).

Arastu Kapur et al., Nonproteasomal targets of the proteasome inhibitors bortezomib and carfilzomib: A link to clinical adverse events. *Clin. Cancer Res*., 17: 2734-43 (2011).

Argiriadi, Binding of alkylurea inhibitors to epoxide hydrolase implicates active site tyrosines in substrate activation. *J. Biol. Chem*. 275(20): 15265-70 (2000).

Aulton (Ed), Pharmaceutics—The Science of the Dosage Form Design, Elsevier, Second Edition, Chapters 1 & 9, pp. 1, 9, 144 (2002).

Bao et al., PR-39 and PR-11 peptides inhibit ischemia-reperfusion injury by blocking proteasome-mediated IκBα degradation. *Am. J. Physiol. Heart Circ. Physiol*. 281: H2612-8 (2001).

Benedetti et al., Versatile and stereoselective synthesis of diamino diol dipeptide isosteres, core units of pseudopeptide HIV protease inhibitors. *J. Org. Chem*. 62: 9348-53 (1991).

Berge et al., Pharmaceutical salts. *J. Pharm. Sci*. 66(1): 1-19 (1977).

Bernier et al. A methionine aminopeptidase-2 Inhibitor, PPI-2458, for the treatment of rheumatoid arthritis. *Proc. Natl. Acad. Sci. USA*, 101(29): 10768-73 (2004).

Bis et al., Defining & addressing solid-state risks after the proof-of-concept stage of pharmaceutical development, *Drug Develop. Deliv*. 32-4 (2011).

(56) References Cited

OTHER PUBLICATIONS

Blackburn et al., Characterization of a new series of non-covalent proteasome inhibitors with exquisite potency and selectivity for the 20S β5-subunit. *Biochem. J.*,430: 461-76 (2010).
Boccadoro et al., Preclinical evaluation of the proteasome inhibitor bortezomib in cancer therapy. *Cancer Cell Intl.* 5(18): (2005).
Bogyo et al., Biochemistry, Proc. Natl. Acad. Sci. USA, 94: 6629-34 (1997).
Bogyo et al., Substrate binding and sequence preference of the proteasome revealed by active-site-directed affinity probes, *Chem. Biol.* 5(6): 307-20 (1998).
Bougauchi et al., Catalytic asymmetric epoxidation of α,β-unsaturated ketones promoted by lanthanoid complexes. *J. Am. Chem. Soc.* 119: 2329-30 (1997).
Brinkley, A brief survey of methods for preparing protein conjugates with dyes, haptens, and cross-linking reagents, *Bioconjug. Chem.* 3: 2-13 (1992).
Brittain et al., Physical characterization of pharmaceutical solids. *Pharma. Res.* 8(8): 963-73 (1991).
Brown et al., Selective reductions. 37. Asymmetric reduction of prochiral ketones with β-(3-pinanyl)-9-borabicyclo[3.3.1]nonane. *J. Org. Chem.* 50: 1384-94 (1985).
Byrn et al., Pharmaceutical solids: A strategic approach to regulatory considerations. *Pharma. Res.* 12(7): 945-54 (1995).
Caira, Crystalline polymorphism of organic compounds, *Topics Curr. Chem.* 198: 163-208 (1998).
Cancer [online], Retrieved from the Internet, URL: <http://www.nlm.nih.gov/medlineplus/cancer.html> [retrieved on Jul. 6, 2007].
Cascio et al., 26S proteasomes and immunoproteasomes produce mainly N-extended versions of an antigenic peptide. *EMBO J.* 20: 2357-66 (2001).
Center for Drug Evaluation and Research, Application No. 21-602, Medical Review, Clinical NDA Review, NDA 21-602 Velcadetm (bortexomib) for injection, Clinical Review, 1-34 (2003).
Center for Drug Evaluation and Research, Application No. 21-602, Medical Review, Clinical NDA Review, NDA 21-602 Velcadetm (bortexomib) for injection, Clinical Review, 1-47 (2003).
Center for Drug Evaluation and Research, Application No. 21-602, Medical Review, Clinical NDA Review, NDA 21-602 Velcadetm (bortexomib) for injection, Clinical Review, 81-125 (2003).
Ciechanover, The ubiquitin-proteasome proteolytic pathway, *Cell*, 79: 13-21 (1994).
Cohen, AIDS mood upbeat-for a change, *Science*, 267: 959-60 (1995).
Collins, Endothelial nuclear factor-κB and the initiation of the atherosclerotic lesion. *Lab. Invest.* 68(5): 499-508 (1993).
Concise Encyclopedia Chemistry, p. 490 (1993).
Corey et al., A general, catalytic, and enantioselective synthesis of α-amino acids, *J. Am. Chem. Soc.* 114: 1906-8 (1992).
Corey et al., Highly enantioselective borane reduction of ketones catalyzed by chiral oxazaborolidines. Mechanism and synthetic implications. *J. Am. Chem. Soc.* 109: 5551-3 (1987).
Craiu et al., Lactacystin and clasto-lactacystin13-lactone modify multiple proteasome 13-subunits and inhibit intracellular protein degradation and major hisotcompatibility complex class I antigen presentation. *J. of Biol. Chem.* 272(20): 13437-45 (1997).
Dana et al., A stereoselective route to hydroxyethylamine dipeptide isosteres. *J. Am. Chem. Soc.* 65: 7609-11 (2000).
Dasmahapatra et al., Carfilzomib interacts synergistically with histone deacetylase inhibitors in mantle cell lymphoma cells in vitro and in vivo. *Mol. Cancer. Ther.* 10: 1686-97 (2011).
Demo et al., Antitumor activity of PR-171, a novel irreversible inhibitor of the proteasome. *Cancer Res.* 67(13): 6383-91 (2007).
Dess et al., A useful 124-5 triacetoxyperiodinane (the Dess-Martin periodinane) for the selective oxidation of primary or secondary alcohols and a variety of related 124-5 species, J. Am. Chem. Soc. 113: 7277-87 (1991).
Dess et al., Readily accessible 12-I-5 oxidant for the conversion of primary and secondary alcohols to aldehydes and ketones. *J. Org. Chem.* 48: 4155-6 (1983).

Diaz-Hernandez et al., Neuronal induction of the immunoproteasome in Huntington's Disease. *J. Neurosci.* 23: 11653-1161 (2003).
Dimopoulos et al., Lenalidomide plus dexamethasone for relapsed or refractory multiple myeloma. *N. Engl. J. Med.* 357(21): 2123-32 (2007).
Dinger et al., Some crystal growing tips, http://xray.chem.ufl.edu/growing%20tips.htm <http://xray.chem.ufl.edu/growing%2520tips.htm>. 3 pages (2006).
Dobler, Total synthesis of (+)-epopromycin B and its analogues-studies on the inhibition of cellulose biosynthesis. *Tetrahedron Lett.* 42(2): 215-8 (2001).
Egerer et al., Tissue-specific up-regulation of the proteasome subunit β5i (LMP7) in Sjogren's Syndrome. *Arthritis Rheum.* 54: 1501-8 (2006).
Elliott et al., The proteasome a new target for novel drug therapies. *Am J Clin Pathol.* 116: 637-46 (2001).
Elofsson et al., Towards subunit-specific proteasome inhibitors: Synthesis and evaluation of peptide α,β-epoxyketones. *Chem. Biol.* 6: 811-22 (1999).
European Search Report, EP 08 16 4241, completed Jan. 22, 2009, 5 pages.
European Search Report, EP 09 00 6228, completed Aug. 25, 2009, 7 pages.
European Search Report, EP 09822636.8, dated Aug. 1, 2012, 6 pages.
Extended European Search Report, EP 12189466.1, dated Jul. 23, 2013, 10 pages.
Extended European Search Report, EP 13167148.9, dated Aug. 2, 2013, 7 pages.
Favit et al., Prevention of β-amyloid neurotoxicity by blockade of the ubiquitin-proteasome protealytic pathway. *J. Neurochem.* 75(3): 1258-63 (2000).
FDA mulls drug to slow late-stage Alzheimers[Online], URL: http://www.cnn.com/2003/H <http://www.cnn.com/2003/H>EALTH/conditions/09/24/alzheimers.drug. ap/index. html [retrieved on Sep. 23, 2003].
Fenteany et al., A β-lactone related to lactacystin induces neurite outgrowth in a neuroblastoma cell line and inhibits cell cycle progression in an osteosarcoma cell line. *Proc. Natl. Acad. Sci. USA*, 91: 3358-62 (1994).
Figueiredo-Pereira et al., The antitumor drug aclacinomycin A, which inhibits the degradation of ubiquitinated proteins, shows selectiveity for the chymotrypsin-like activity of the bovine pituitary 20 S proteasome. *J. Biological Chem.* 271(2): 16455-9 (1996).
First Vitality, Alzheimer's & Senile Dementia, <http://www.lstvitality.co.uk/health/alzheimers/>carnosine_proteasomal_alzheimers.htm, p. 1 (2008).
Fox et al., Organic Chemistry, Publisher: Jones & Bartlett Pub, Published Jun. 15, 2004, Sec. 5-6, pp. 177-178, ISBN-10: 0763721972, ISBN-13: 9780763721978.
Gan et al., Identification of cathepsin B as a mediator of neuronal death induced by A-activated microglial cells using a functional genomics approach. *J. Biol. Chem.* 279: 5565-72 (2004).
Gao et al., Inhibition of ubiquitin-proteasome pathway-mediated IκBα degradation by a naturally occurring antibacterial peptide. *J. Clin. Invest.* 106: 439-48 (2000).
Garcia-Echeverria, Peptide and peptide-like modulators of 20S proteasome enzymatic activity in cancer cells, *Intl. J. Peptide Res. Ther.* 12(1): 49-64 (2006).
Garrett et al., Selective inhibitors of the osteoblast proteasome stimulate bone formation in vivo and in vitro. *J. Clin. Invest.* 111: 1771-82 (2003).
Gennaro, Remington: Practice of the Science of Pharmacy, 19th Edition, Mack Publishing Company, Chapter 83, pp. 1447-1462 (1995).
Golub et al., Molecular classification of cancer: Class discovery and class prediction by genes expression monitoring. *Science*, 286: 531-7 (1999).
Gonzales et al., Pain relief in chronic pancreatitis by pancreaticojejunostomy. An institutional experience. *Arch. Med. Res.* 28(3): 387-90 (1997).

(56) References Cited

OTHER PUBLICATIONS

Gordon et al., 1207 results of study PX-171-007 a phase lb/2 study of carfilzomib, a selective proteasome inhibitor, in patients with selected advanced metastatic solid tumors. *Eur. J. Cancer Suppl.* 7(2): 122-3 (2009).
Graz University of Technology, Database of fluorescent dyes properties and applications WWW.Fluorophonres.org <http://WWW.Fluorophonres.org>, 33 pgs, Exhibit B to response filed with US Patent office on Sep. 16, 2008 for U.S. Appl. No. 11/254,541 (now abandoned).
Green et al., Protective groups in organic synthesis, 2nd Ed., Wiley & Sons, Inc., New York (1991).
Griffith et al., Molecular recognition of angiogenesis inhibitors fumagillin and ovalicin by methionine aminopeptidase. *Proc. Natl. Acad. Sci. USA*, 95: 15183-8 (1998).
Groettrup et al., Selective proteasome inhibitors: Modulators of antigen presentation? *Drug Discovery Today*, 4(2): 63-71 (1999).
Groll et al., Crystal structure of epoxomicin: 20S proteasome reveals a molecular basis for selectivity of ré, âé-epoxyketone proteasome inhibitors. *J. Am. Chem. Soc.* 122: 1237-8 (2000).
Gura, Systems for identifying new drugs are often faulty. *Science*, 278(5340): 1041-2 (1997).
Hanada et al,. Epoxomicin, a new antitumor agent of microhial origin. *J. Antihiotics*, 45(11): 1746-52 (1992).
Hanson et al., Synthesis of new dipeptide analogues containing novel ketovinyl and hydroxyethylidene isosteres via Grignard addition to chiral α-amino aldehydes. *J. Org. Chem.* 50: 5399-401 (1985).
Harding et al., Novel dipeptide aldehydes are proteasome inhibitors and block the MHC-1 antigen-processing pathway. *J. Immunol.* 155: 1767-75 (1995).
Hardy, The secret life of the hair follicle. *Trends Genet.* 8: 55-61 (1992).
Harris et al., Effects of transforming growth factor 13 on bone nodule formation and expression of bone morphogenetic protein 2, osteocalcin, osteopontin, alkaline phosphatase, and type I collagen mRNA in long-term cultures of fetal rat calvarial osteoblasts. *J. Bone Miner. Res.* 9(6): 855-63 (1994).
Haugland, Coupling of monoclonal antibodies with fluorophores. *Methods Mol. Biol.* 45: 205-21 (1995).
*Hawley's Condensed Chemical Dictionary*, p. 594 (1993).
Hilfiker, Ed., *Polymorphism in the Pharmaceutical Industry*, pp. 12-15 (2006).
Hoffman et al., Highly stereoselective synthesis of syn- and anti-1,2-amino alcohols. *J. Org. Chem.* 67:1045-1056 (2002).
Holbeck et al., Analysis of food and drug administration—Approved anticancer agents in the NC160 panel of human tumor cell lines. *Mol. Cancer Ther.* 9: 1451-60 (2010).
Huff, HIV protease: A novel chemotherapeutic target for AIDS. *J. Med. Chem.* 34(8): 2305-14 (1991).
International Preliminary Report on Patentability for corresponding PCT Application No. PCT/US2005/012740, issued Oct. 19, 2006, 11 pgs.
International Preliminary Report on Patentability for corresponding PCT Application No. PCT/US2005/016335, issued Nov. 14, 2006, 11 pgs.
International Preliminary Report on Patentability for International Application No. PCT/US2008/005997, dated Nov. 10, 2009.
International Preliminary Report on Patentability for PCT/US2005/017000, issued Nov. 21, 2006, 12 pages.
International Preliminary Report on Patentability for PCT/US2005/028246, issued Feb. 6, 2007, 8 pages.
International Preliminary Report on Patentability for PCT/US2005/037966, issued Apr. 24, 2007, 12 pages.
International Preliminary Report on Patentability for PCT/US2005/044451, issued Jun. 13, 2007, 8 pages.
International Preliminary Report on Patentability for PCT/US2008/005997, issued Nov. 10, 2009, 7 pages.
International Preliminary Report on Patentability for PCT/US2008/011443, issued Apr. 7, 2010, 12 pages.
International Preliminary Report on Patentability for PCT/US2010/056395, mailed May 24, 2012, 8 pages.
International Preliminary Report on Patentability for PCT/US2011/026629, dated Sep. 4, 2012, 11 pages.
International Preliminary Report on Patentability PCT/US2007/014427, issued Dec. 22, 2008, 8 pages.
International Preliminary Report on Patentability PCT/US2009/061498, dated May 5, 2011, 9 pages.
International Preliminary Report on Patentability PCT/US2011/031436, dated Oct. 9, 2012, 5 pages.
International Search Report (Partial) for PCT/US2008/011443, dated Dec. 9, 2008, 6 pages.
International Search Report and Written Opinion for corresponding PCT Application No. PCT/US2005/012740, mailed Jan. 9, 2006, 16 pgs.
International Search Report and Written Opinion for corresponding PCT Application No. PCT/US2005/016335, mailed Jan. 2, 2006, 17 pgs.
International Search Report and Written Opinion for PCT/US2007/014427, mailed Dec. 3, 2007, 12 pages.
International Search Report and Written Opinion for PCT/US2010/056395, mailed Mar. 15, 2011, 10 pages.
International Search Report and Written Opinion for PCT/US2011/026629, mailed Jun. 30, 2011, 18 pages.
International Search Report and Written Opinion for PCT/US2011/031436, mailed Nov. 28, 2011, 5 pages.
International Search Report and Written Opinion of the International Searching Authority for PCT/US2005/017000, mailed Feb. 3, 2006, 12 pages.
International Search Report and Written Opinion of the International Searching Authority for PCT/US2005/028246, mailed Jan. 19, 2006, 11 pages.
International Search Report and Written Opinion of the International Searching Authority for PCT/US2005/037966, mailed Jan. 24, 2006, 17 pages.
International Search Report and Written Opinion of the International Searching Authority for PCT/US2005/044451, mailed May 2, 2006, 12 pages.
International Search Report and Written Opinion of the International Searching Authority for PCT/US2006/043503, mailed Feb. 19, 2007, 17 pages.
International Search Report and Written Opinion of the International Searching Authority for PCT/US2008/005997, mailed Nov. 7, 2008, 8 pages.
International Search Report and Written Opinion of the International Searching Authority for PCT/US2008/011443, mailed Mar. 25, 2009, 16 pages.
International Search Report and Written Opinion of the International Searching Authority for PCT/US2010/028126, mailed Jun. 9, 2010, 13 pages.
International Search Report and Written Opinion of the International Searching Authority for PCT/US2012/055127, mailed Dec. 18, 2012, 10 pages.
International Search Report and Written Opinion of the International Searching Authority for PCT/US2013/040127, mailed Oct. 22, 2013, 15 pages.
International Search Report for PCT/US2009/061498, mailed Dec. 10, 2009, 5 pages.
Iqbal et al., Potent α-ketocarbonyl and boronic ester derived inhibitors of proteasome. *Bioorg. Med. Chem. Lett.* 6: 287-90 (1996).
Iqbal et al., Potent inhibitors of proteasome. *J. Med Chem.* 38: 2276-7 (1995).
Ivanisevic et al., Uses of X-ray powder diffraction in the pharmaceutical Industry. *Pharmaceutical Sciences Encyclopedia: Drug Discovery, Development, and Manufacturing*, Edited by Shayne C. Gad, pp. 1-42 (2010).
Jacobsen et al., Asymmetric dihydroxylation via ligand-accelerated catalysis, *J. Am. Chem. Soc.* 110: 1968-70 (1988).
Jain, Delivery of molecular medicine to solid tumors. *Science*, 271(5252): 1079-80 (1996).
Jones et al., Total synthesis of the immunosuppressant (−)-FK-506. *J. Am. Chem. Soc.* 111: 115-79 (1989).

(56) References Cited

OTHER PUBLICATIONS

Jung et al., Melatonin in cancer management: Progress and promise. *Cancer Res.* 66(22): 9789-93 (2006).

Kessler et al., Extended peptide-based inhibitors efficiently target the proteasome and reveal overlapping specificities of the catalytic 13-subunits. *Chem. Biol.* 8(9): 913-29 (2001).

Khan et al., Immunoproteasomes largely replace constitutive proeatsomes during an antiviral and antibacterial immune response in the liver. *J. Immunol.* 167: 6859-68 (2001).

Kijima et al., Trapoxin, an antitumor cyclic tetrapeptide, is an irreversible inhibitor of mammalian histone deacetylase. *J. Biol. Chem.* 268(30): 22429-35 (1993).

Kim et al., Proteasome inhibition by the natural products epoxomicin and dihydroeponemycin: insights into specificity and potency. *Bioorg. Med. Chem. Lett.* 9: 3335-40 (1999).

Kisselev et al., Proteasome inhibitors: From research tools to drug candidates. *Chem. Biol.* 8(8): 739-58 (2001).

Kojima et al., Two-way cleavage of 13-amyloid protein precursor by multicatalytic proteinase. *Fed. Eur. Biochem. Soc.* 304: 57-60 (1992).

Koong et al., Hypoxia causes the activation of nuclear factor-κB through the phosphorylation of IκBα on tyrosine residues. *Cancer Res.* 54: 1425-30 (1994).

Koong et al., Hypoxic activation of nuclear factor-κB is mediated by a Ras and Raf signaling pathway and does not involve MAP kinase (ERK1 or ERK2)1. *Cancer Res.* 54:5273-5279, Oct. 15, 1994.

Kreidenweiss et al., Comprehensive study of proteasome inhibitors against Plasmodium falciparum laboratory strains and field isolates from Gabon. *Malar. J.*, 7(187): 1-8 (2008).

Krise et al., A novel prodrug approach for tertiary amines: Synthesis and preliminary evaluation of N-phosphonooxymethyl prodrugs. *J. Med. Chem.* 42: 3094-100 (1999).

Kuhn et al., Potent activity of carfilzomib, a novel, irreversible inhibitor of the ubiquitin-proteasome pathway, against preclinical models of multiple myeloma. *Blood*, 110(9): 3281-90, prepublished online: Jun. 25, 2007.

Kumatori et al., Abnormally high expression of proteasomes in human leukemic cells. *Proc. Natl. Acad. Sci. USA*, 87: 7071-5 (1990).

Le Blanc et al., Growth in vivo and prolongs survival in a murine model proteasome inhibitor PS-341 inhibits human myeloma cell. *Cancer Res.* 62: 4996-5000 (2002).

Lecker et al., Multiple types of skeletal muscle atrophy involve a common program of changes in gene expression. *FASEB J.* 18: 39-51 (2004).

Lee et al., Proteasome inhibitors: Valuable new tools for cell biologists. *Trends in Cell Biol.* 8: 397-403 (1988).

Liang et al., Screening polymorphic form of drug substances by using generalized crystallization techniques. Master's thesis, Institute of Chemical Engineering, National Taipei University of Technology, dated May 2007.—English translation of abstract and section 3.1.1.2.

Liang et al., Synthesis of cryptophycin 52 using the sharpless asymmetric dihydroxylation: Diol to epoxide transformation optimized for a base-sensitive substrate. *J. Am. Chem. Soc.*65: 3143-7 (2000).

Lin et al., Alteration of substrate and inhibitor specificity of feline immunodeficiency virus protease. *J. Virol.* 74(10): 4710-20 (2000).

Loftsson et al., Pharmaceutical applications of cyclodextrins. 1. Drug solubilization and stabilization. *J. Pharma. Sci.*, American Pharmaceutical Association, 85(10): 1017-25 (1996).

Luke et al., Review of the basic and clinical pharmacology of sulfobutylether-β-0Cyclodextrin (SBECD). *J. Pharma. Sci.* 99: 3291-301 (2010).

MacAry et al., Mobilization of MHC class I molecules from late endosomes to the cell surface following activation of CD34-derived human Langerhans cells. Proc. Natl. Acad. Sci. 98: 3982-7 (2001).

Mandel et al., Neuroprotective strategies in Parkinson's Disease. *CNS Drugs*, 17(10): 729-62 (2003).

Marx et al., Reactivity-selectivity in the Swern Oxidation of alcohols using dimethyl sulfoxide-oxalyl chloride. *J. Org. Chem.* 49: 788-93 (1984).

McGraw-Hill Dictionary of Chemical Terms, p. 282 (1990).

Meng et al., Eponemycin exerts its antitumor effect through the inhibition of proteasome function. *Cancer Res.* 59: 2798-801 (1999).

Meng et al., Epoxomicin, a potent and selective proteasome inhibitor, exhibits in vivo anti-inflammatory activity. *Proc. Natl. Acad. Sci. USA*, 96: 10403-8 (1999).

Min et al., Bortezomib in combination with conventional chemotherapeutic agents for multiple myeloma compared with bortezomib alone. *Jap. J. Clin. Oncol.* 37(12): 961-8 (2007).

Mishto et al., Immunoproteasome and LMP2 polymorphism in aged and Alzheimer's disease brains. *Neurobiol. Aging*, 27: 54-66 (2006).

Molecular biology and biotechnology a comprehensive desk reference: Edited by R A Meyers. pp. 658-664. VCH, Weinheim, Germany, 1995, DM89 ISBN 1-56081-925-1.

Molecular Probes, Inc., Introduction to Fluorescence techniques, invitrogen detection technologies, 11 pgs, Molecular Probes, Inc. (2007), Exhibit A to response filed with US Patent Office on Sep. 16, 2008 for U.S. Appl. No. 11/254,541 (now abandoned).

Morissette et al., High-thoughput crystallization: polymorphs, salts, co-crystals and solvates of pharmaceutical solids, *Adv. Drug Deliv. Rev. Amsterdam*, 56(3): 276 (2004).

Morris, Structural aspects of hydrates and solvates in polymorphism in pharmaceutical solids. *Polymorphism in Pharmaceutical Solids*, Ed H. G. Nbrittain, Marcel Dekker, New York, pp. 125-81 (1999).

Muchamuel et al., A selective inhibitor of the immunoproteasome subunit NMP7 blocks cytokine production and attenuates progression of experimental arthritis. *Nat. Med.* 15:781-7 (2009).

Myung et al., Lack of proteasome active site allostery as revealed by subunit-specific inhibitors. *Molec. Cell*, 7(2): 411-20 (2001).

Myung et al., The ubiquitin-proteasome pathway and proteasome inhibitors. *Med. Res. Rev.* 21(4): 245-73 (2001).

Nemoto et al., Catalytic asymmetric epoxidation of enones using La-BINOL-Triphenylarsine oxide complex: Structural determination of the asymmetric catalyst. *J. Am. Chem. Soc.* 123: 2725-32 (2001).

Newman et al., Solid-state analysis of the active pharmaceutical ingredient in drug products. *Drug Disc. Today*, 8(19): 898-905 (2003).

Oishi et al., Diastereoselective synthesis of new psi '(E)-CH=CMel- and psi '(Z)-CH=CMel-type alkene dipeptide isosteres by organocopper reagents and application to conformationally restricted cyclic RGD peptidomimetics. *J. Org. Chem.* 67: 6162-73 (2002).

Orlowski et al., Phase I trial of the proteasome inhibitor PS-341 in patients with refractory hematologic malignancies. *J. Clin. Oncol.* 20(22): 4420-7 (2002).

Orlowski et al., Proteasome inhibitors in cancer therapy: Lessons from the first decade. *Clin. Cancer Res.* 14:1649-65 (2008).

Overkleeft et al., Solid phase synthesis of peptide vinyl sulfone and peptide expoxyketone proteasome inhibitors. *Tetrahedron Lett.* 41(32): 6005-9 (2000).

Palombella et al., The ubiquitin-proteasome pathway is required for processing the NF-κB1 precursor protein and the activation of NF-κB. *Cell*, 78: 773-85 (1994).

Paoluzzi et al., Targeting Bcl-2 family members with the BH3 mimetic AT-101 markedly enhances the therapeutic effects of chemotherapeutic agents in in vitro and in vivo models of B-cell lymphoma. *Blood*, 111(11): 5350-8 (2008).

Paugam et al., Characterization and role of protozoan parasite proteasomes. *Trends Parasitol.* 19: 55-9 (2003).

Pivazyan et al., Inhibition of HIC-1 protease by a boron-modified polypeptide. *Biochem. Pharm.* 60: 927-36 (2000).

Polymorphism in Pharmaceutical Solids, edited by Brittain, Marcel Dekker Inc., p. 228-229, 236 (1999).

Pye et al., Proteasome inhibition ablates activation of NF-KB in myocardial reperfusion and reduces reperfusion of injury. *Am. J. Physiol. Heart Circ. Physiol.* 284: H919-26 (2003).

Qureshi et al., The proteasome as a lipopolysaccharide-binding protein in macrophages: Differential effects of proteasome inhibition on lipopolysaccharide-induced signaling events. *J. Immunol.* 171: 1515-25 (2003).

Raw et al., Regulatory considerations of pharmaceutical solid polymorphism in Abbreviated New Drug Applications (ANDAs). *Adv. Drug Deliv. Rev.* 56: 397-414 (2004).

(56) References Cited

OTHER PUBLICATIONS

Reidlinger et al., Catalytic properties of 26 S and 20 S proteasomes and radiolabeling of MB 1, LMP7, and C7 subunits associated with trypsin-like and chymotrypsin-like activities. *J. Biol Chem.* 272(40): 24899-905 (1997).

Roccaro et al., Selective inhibition of chymotrypsin-like activity of the immunoproteasome and constitutive proteasome in Waldenstrom macroglobulimia. *Blood*, 115: 4051-60 (2010).

Rossi et al., Proteasome inhibitors in cancer therapy: death by indigestion. *Cell Death Differ*. 1255-7 (2005).

Rouhi, Chemical & Engineering News, p. 32-35, Feb. 24, 2004.

Safadi et al., Phosphoryloxymet hyl carbarnates and carbonates-novel water-soluble prodrugs for amines and hindered alcohols. *Pharma. Res.* 10(9): 1350-5 (1993).

Schwarz et al., The selective proteasome inhibitors lactacystin and epoxomicin can be used to either up- or down-regulate antigen presentation at nontoxic doses. *J. Immunol.* 164: 6148-57 (2000).

Shah et al., Analytical techniques for quantification of amorphous/crystalline phases in pharmaceutical solids. *J. Pharm. Sci.* 95(8): 1641-65 (2006).

Shao et al., A new asymmetric synthesis of α-methylcysteines via chiral aziridines. *J. Org. Chem*.60: 790-1 (1995).

Sharpless et al., High stereo- and regioselectivities in the transition metal catalyzed epoxidations of olefinic alcohols by tert-butyl hydroperoxide. *J. Am. Chem. Soc.* 95: 6136-7 (1973).

Shoemaker, The NCI60 human tumour cell line anticancer drug screen. *Nat. Rev. Cancer*, 6: 813-23 (2006).

Simsek et al., Hepatitis B virus large and middle glycoproteins are degraded by a proteasome pathway in glucosidase-inhibited cells but not in cells with functional glucosidase enzyme. *J. Virol.* 79(20): 12914-20 (2005).

Sin et al., Eponymycin analogues: Syntheses and use as probes of angiogenesis, *Bioorg. Med. Chem. Lett*. 6(8): 1209-17 (1998).

Sin et al., Total synthesis of the potent proteasome inhibitor epoxomicin: a useful tool for understanding proteasome biology. *Bioorg. Med. Chem. Lett.* 9: 2283-8 (1999).

Singhal et al., Drug polymorphism and dosage form design: A practical perspective. *Adv. Drug Deliv. Rev.* 56: 335-47 (2004).

Spaltenstein et al., Design and synthesis of novel protease inhibitors. Tripeptide α',β'-epoxyketones as nanomolar inactivators of the proteasome. *Tetrahedron Lett.* 37: 1343-6 (1996).

Stahl et al., Handbook of Pharmaceutical Salts: Properties, Selection, and Use. pp. 198-200 (2002).

Stein et al., Kinetic characterization of the chymotryptic activity of the 20S proteasome. *Biochemistry*, 35: 3899-908 (1996).

Stoklosa et al., Prospects for p53-based cancer therapy. *Acta Biochim Pol.* 52(2): 321-8 (2005).

Strickley, Solubilizing excipients in oral and injectable formulations. *Pharma. Res.* 21(2): 201-30 (2004).

Sun et al., Inhibition of acute graft-versus-host disease with retention of graft-versus-tumor effects by the proteasome inhibitor bortezomib. *Proc. Natl. Acad. Sci. USA*, 101(2): 8120-5 (2004).

Szalay et al., Ongoing coxsackievirus myocarditis is associated with increased formation and activity of myocardial immunoproteaseomes. *Am. J. Pathol.* 168(5): 1542-52 (2006).

Tawa et al., Inhibitors of the proteasome reduce the accelerated proteolysis in atrophying rat skeletal muscles., *J. Clin. Invest.* 100: 197-203 (1997).

Terato et al., Induction of arthritis with monoclonal antibodies to collagen. *J. Immunol.* 148(7): 2103-8 (1992).

Thanos et al., NF-κB: A lesson in family values. *Cell*, 80: 529-32 (1995).

Thompson, Cyclodextrins-enabling excipients: Their present and future use in pharmaceuticals. *Crit. Rev. Therapeut. Drug Carr. Syst.* 14(1): 1-104 (1997).

Tong, Applications of complexation in the formulation of insoluble compounds. R. Liu, Ed., pp. 111-139 (2000).

Traenckner et al., A proteasome inhibitor prevents activation of NF-κB and stabilizes a newly phosphorylated form of IκB-α that is still bound to NF-κB. *EMBO J.* 13: 5433-41 (1994).

Tu et al., An efficient assymettric epoxidation method for trans-olefins mediated by a fructose-derived ketone. *J. Am. Chem. Soc.* 118: 9806-7 (1996).

U.S. Pharmacopia #23, National Formulary #18, p. 1843-4 (1995).

U.S. Appl. No. 60/928,758, "Compounds for Enzyme Inhibition", filed May 10, 2007.

Vogel's textbook of practical organic chemistry, 5th Ed. See p. 135, 2.20 Recrystallisation Techniques and p. 141, 2nd paragraph onwards, Feb. 1996.

Voskoglou-Nomikos, Clinical predictive value of the in vitro cell line, human xenograft, and mouse allograft preclinical cancer models. *Clin. Cancer Res.* 9(11): 4227-39 (2003).

Wang et al., A new type of ketone catalyst for asymmetric epoxidation. *J. Org. Chem.* 62: 8622-3 (1997).

Watanabe et al., Synthesis of boronic acid derivatives of tyropeptin: Proteasome inhibitors. *Bioorg. & Med. Chem.*, 19(8): 2343-5 (2009).

WebMD, HIV and AIDS, <www.webmd.com/hiv-aids/guide/sexual-health-aids<http://www.webmd.com/hiv-aids/guide/sexual-health-aids>> pp. 1-2 (2009).

Wilson et al., Novel disease targets and management approaches for diffuse large B-cell lymphoma. *Leuk. Lymph.* 51(suppl. 1): 1-10, abstract only (2010).

Wipf et al., Methyl- and (trifluoromethyl)alkene peptide isosteres: Synthesis and evaluation of their potential as β-turn promoters and peptide mimetics. *J. Org. Chem.* 63: 6088-9 (1998).

Xu et al., Mutations in the tumor suppressors Smad2 and Smad4 inactivate transforming growth factor β signaling by targeting Smads to the ubiquitin-proteasome pathway. *Proc. Natl. Acad. Sci. USA*, 97(9): 4820-5 (2000).

Yang et al., Pharmacokinetics, pharmacodynamics, metabolism, distribution, and excretion of carfilzomib in rats. *Drug Metabol. Disp.* 39: 1873-82 (2011).

Yu et al., The ubiquitin-proteasome system facilitates the transfer of murine coronavirus from endosome to cytoplasm during virus entry. *J. Virol.* 79(1): 644-8 (2005).

Zhou et al., Design and synthesis of an orally bioavailable and selective peptide epoxyketone proteasome inhibitor (PR-047). *Med. Chem.* 52 (9): 3028-38 (2009).

Zhu et al., 3D-QSAR studies of boron-containing dipeptides as proteasome inhibitors with CoMFA and CoMSIA methods. *Eur. J. Med. Chem.* 44(4):1486-99 (2009).

Zhu et al., Design, synthesis and biological evaluation of tripeptide boronic acid proteasome inhibitors. *Bioorg. Med. Chem.* 17(19): 6851-61 (2009).

Zollner et al., Proteasome inhibition reduces superantigen-mediated T cell activation and the severity of psoriasis in a SCID-hu model. *J. Clin. Invest.* 109(5): 671-9 (2002).

CRYSTALLINE TRIPEPTIDE EPOXY KETONE PROTEASE INHIBITORS

RELATED APPLICATIONS

This application claims the benefit of priority to U.S. Provisional Application Ser. No. 61/162,196, filed Mar. 20, 2009, and U.S. Provisional Application Ser. No. 61/180,561, filed May 22, 2009. The specifications of the foregoing applications are hereby incorporated by reference in their entirety.

BACKGROUND OF THE INVENTION

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multicatalytic protease, which cleaves proteins into short peptides through the action of its three major proteolytic activities. While having a general function in intracellular protein turnover, proteasome-mediated degradation also plays a key role in many processes such as major histocompatibility complex (MHC) class I antigen presentation, apoptosis, cell growth regulation, NF-κB activation, antigen processing, and transduction of pro-inflammatory signals.

The 20S proteasome is a 700 kDa cylindrical-shaped multicatalytic protease complex comprised of 28 subunits organized into four rings. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation expose amino-terminal threonine residues, which serve as the catalytic nucleophiles. The subunits responsible for catalytic activity in proteasomes thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three interferon-γ-inducible β subunits (LMP7, LMP2 and MECL1), which replace their normal counterparts, $\beta_5$, $\beta_1$ and $\beta_7$ respectively, thus altering the catalytic activities of the proteasome. Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. The major proteasome proteolytic activities appear to be contributed by different catalytic sites, since inhibitors, point mutations in β subunits and the exchange of γ interferon-inducing β subunits alter these activities to various degrees.

Improved compositions and methods for preparing and formulating proteasome inhibitor(s) are needed.

SUMMARY OF THE INVENTION

One aspect of the invention relates to crystalline compounds having a structure of Formula (I) or a pharmaceutically acceptable salt thereof,

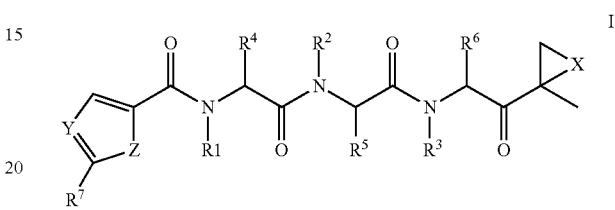

wherein
X is O, NH, or N-alkyl, preferably O;
Y is N, S, or $C(R^8)_2$, preferably NH;
Z is NH, N-alkyl, O, S or $C(R^8)_2$, preferably S;
$R^1$, $R^2$, and $R^3$ are hydrogen;
each of $R^4$, $R^5$, $R^6$, $R^7$ and $R^8$ is independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether, preferably $R^4$, $R^5$ and $R^6$, are independently selected from $C_{1-6}$thioether, $C_{1-6}$hydroxyalkyl, and $C_{1-6}$aralkyl and $R^7$ is $C_{1-6}$alkyl, more preferably, $R^4$ and $R^5$ are $C_{1-6}$thioether, and $R^7$ is $C_{1-6}$alkyl.

DETAILED DESCRIPTION OF THE INVENTION

Figure 1:
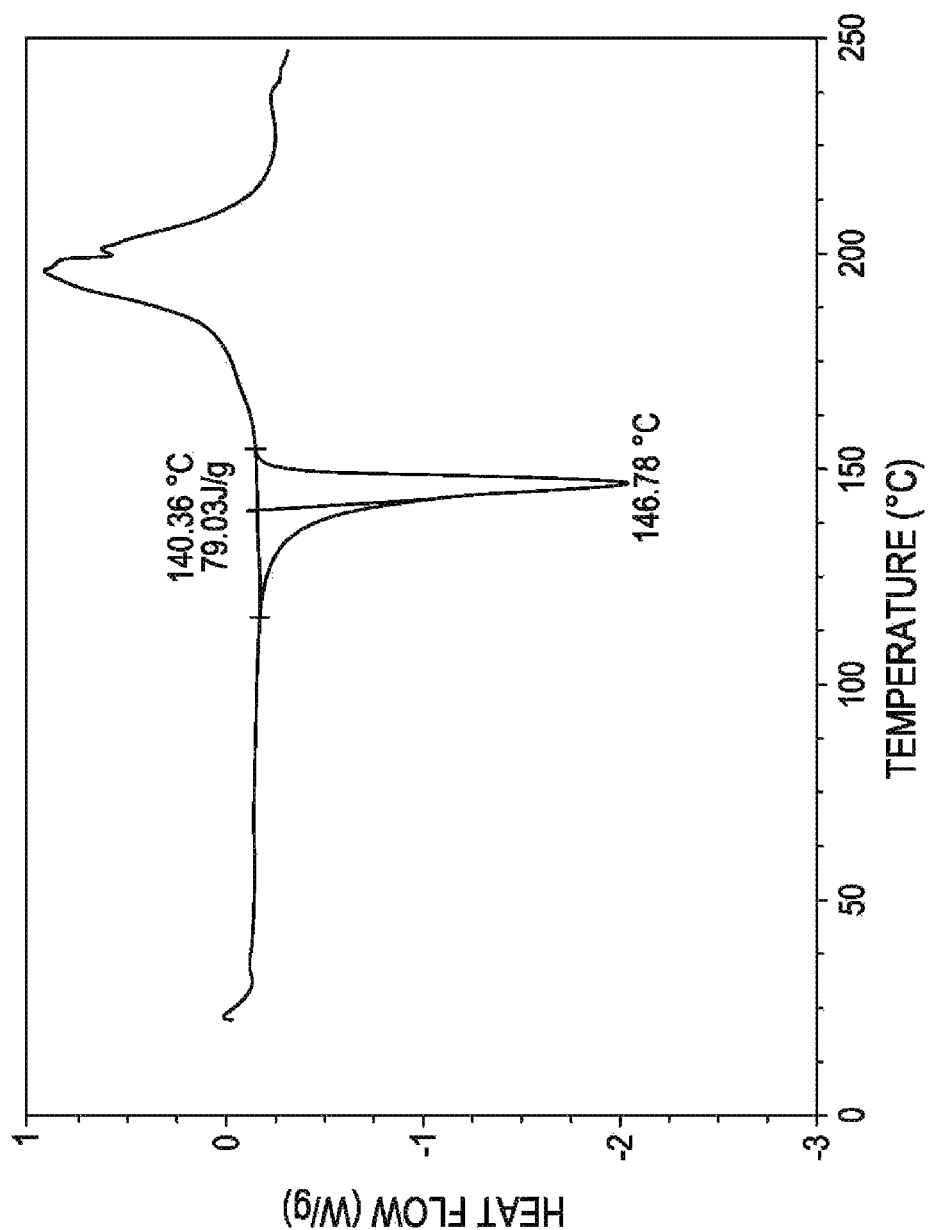
FIG. 1 shows a DSC (differential scanning calorimetry) thermogram of crystalline compound 1.

In certain embodiments, the invention relates to crystalline compounds having a structure of Formula (I) or a pharmaceutically acceptable salt thereof,

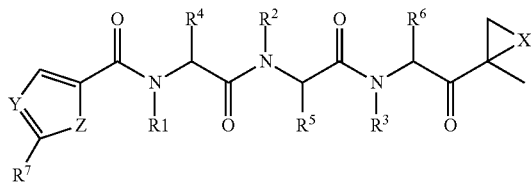

wherein
X is O, NH, or N-alkyl, preferably O;
Y is NH, N-alkyl, O, S, or $C(R^8)_2$, preferably NH;
Z is NH, N-alkyl, O, S or $C(R^8)_2$, preferably S;
$R^1$, $R^2$, and $R^3$ are hydrogen;
each of $R^4$, $R^5$, $R^6$, $R^7$ and $R^8$ is independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether, preferably $R^4$, $R^5$ and $R^6$, are independently selected from $C_{1-6}$thioether, $C_{1-6}$hydroxyalkyl, and $C_{1-6}$aralkyl and $R^7$ is $C_{1-6}$alkyl, more preferably, $R^4$ and $R^5$ are $C_{1-6}$thioether, and each $R^7$ is $C_{1-6}$alkyl In certain embodiments, the invention relates to a crystalline compound of Formula (II)

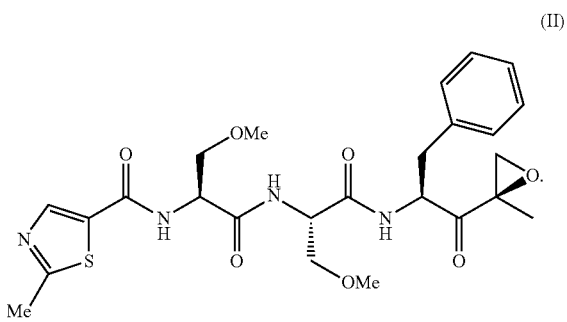 [SMILES: COC[C@H](NC(=O)c1cnc(C)s1)C(=O)N[C@@H](COC)C(=O)N[C@@H](Cc1ccccc1)C(=O)[C@@]1(C)CO1]

In certain embodiments, the invention relates to a method for the preparation of a crystalline compound of Formula (I) or (II), comprising one or more of: (i) preparing the amorphous compound, e.g., according to U.S. patent application Ser. No. 11/595,804; (ii) dissolving the amorphous compound in an organic solvent; (iii) bringing the solution to supersaturation; (iv) isolating the crystals, e.g., by filtering the crystals, by decanting fluid from the crystals, or by any other suitable separation technique; and (v) washing the crystals. In certain embodiments, preparation further comprises inducing crystallization. In certain embodiments, preparation further comprises drying, preferably under reduced pressure, such as under vacuum pressure.

In certain embodiments, the amorphous compound may be dissolved in a solvent selected from acetonitrile, ethyl acetate, heptanes, hexanes, isopropyl acetate, methanol, methylethyl ketone, tetrahydrofuran, toluene, and water, or any combination thereof. In certain embodiments, the amorphous compound of Formula (II) may be dissolved in an organic solvent selected from acetonitrile, heptanes, hexanes, methanol, tetrahydrofuran, and toluene, or any combination thereof. In certain preferred embodiments, the organic solvent is toluene, tetrahydrofuran, or acetonitrile, preferably acetonitrile or toluene.

In certain embodiments, bringing the solution to supersaturation comprises the slow addition of an anti-solvent, such as water, heptanes, hexanes or another polar or non-polar liquid miscible with the organic solvent, allowing the solution to cool (with or without seeding the solution), reducing the volume of the solution, or any combination thereof. In certain embodiments, bringing the solution to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the method further comprises inducing precipitation or crystallization. In certain embodiments, inducing precipitation or crystallization comprises secondary nucleation, wherein nucleation occurs in the presence of seed crystals or interactions with the environment (crystallizer walls, stirring impellers, sonication, etc.).

In certain embodiments, washing the crystals comprises washing with a liquid selected from anti-solvent, acetonitrile, heptanes, hexanes, methanol, tetrahydrofuran, toluene, water, or a combination thereof. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene.

In certain embodiments, washing the crystals comprises washing the crystalline compound of Formula (II) with a mix of tetrahydrofuran and an alkane solvent, such as hexanes or heptanes, or with a mix of acetonitrile and water. In certain embodiments, washing the crystals comprises washing the crystalline compound of Formula (II) with toluene. In preferred such embodiments, the toluene is cooled prior to washing.

In certain embodiments, a crystalline compound of Formula (II) is substantially pure. In certain embodiments, the melting point of the crystalline compound of Formula (II) is in the range of about 135 to about 160° C., about 140 to about 155° C., about 145 to about 150° C., or even about 147 to about 149° C., e.g., about 149° C.

In certain embodiments, the DSC of a crystalline compound of Formula (II) has a sharp endothermic maximum at about 147° C., e.g., resulting from melting and decomposition of the crystalline form as shown in FIG. 1.

Figure 2:
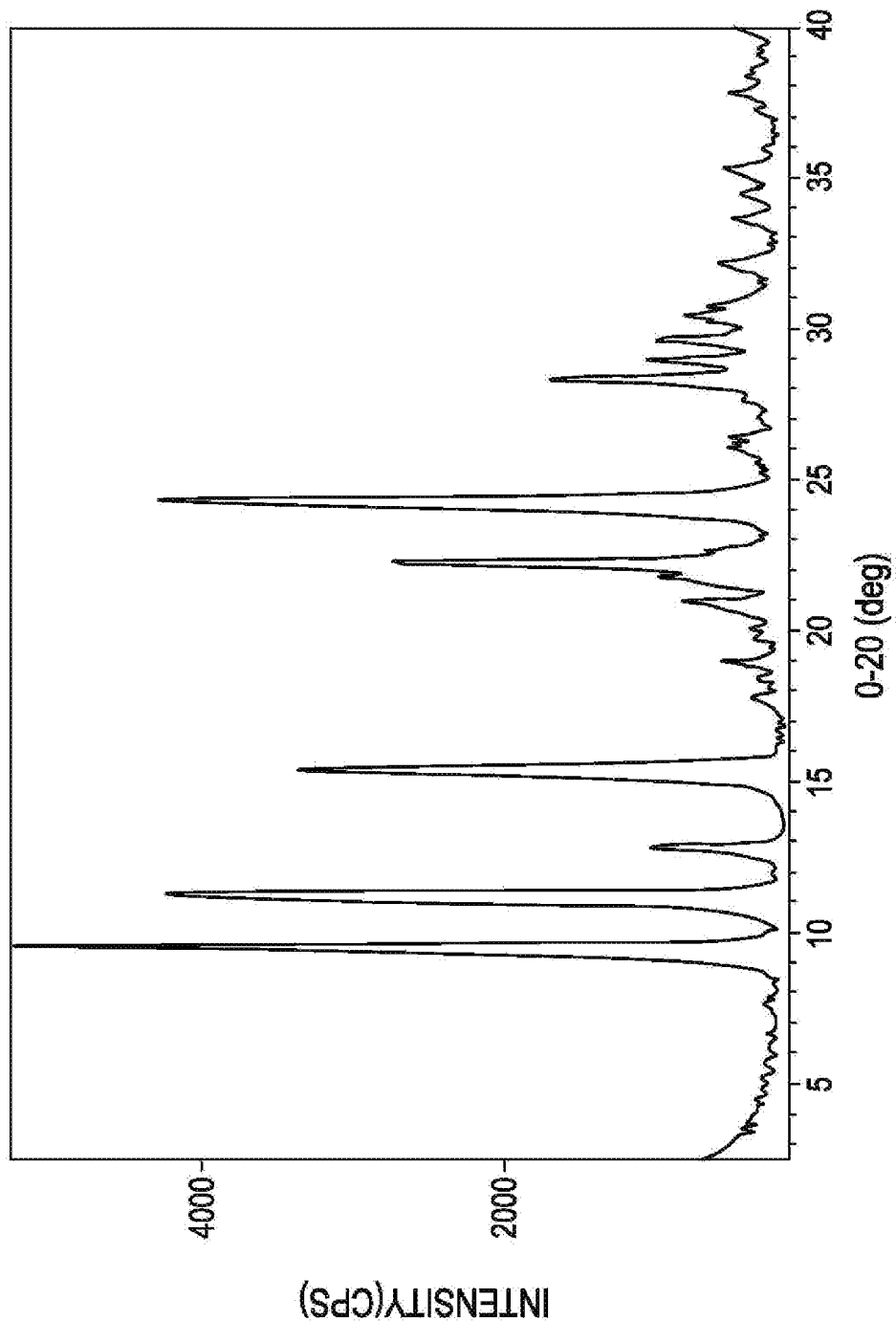
FIG. 2 shows an XRPD (X-ray powder diffraction) pattern of crystalline compound 1.

In certain embodiments, the X-ray powder pattern of a crystalline compound of Formula (II) is (θ-2θ°): 8.94; 9.39; 9.76; 10.60; 11.09; 12.74; 15.27; 17.74; 18.96; 20.58; 20.88; 21.58; 21.78; 22.25; 22.80; 24.25; 24.66; 26.04; 26.44; 28.32; 28.96; 29.65; 30.22; 30.46; 30.78; 32.17; 33.65; 34.49; 35.08; 35.33; 37.85; 38.48 as shown in FIG. 2.

Figure 3:
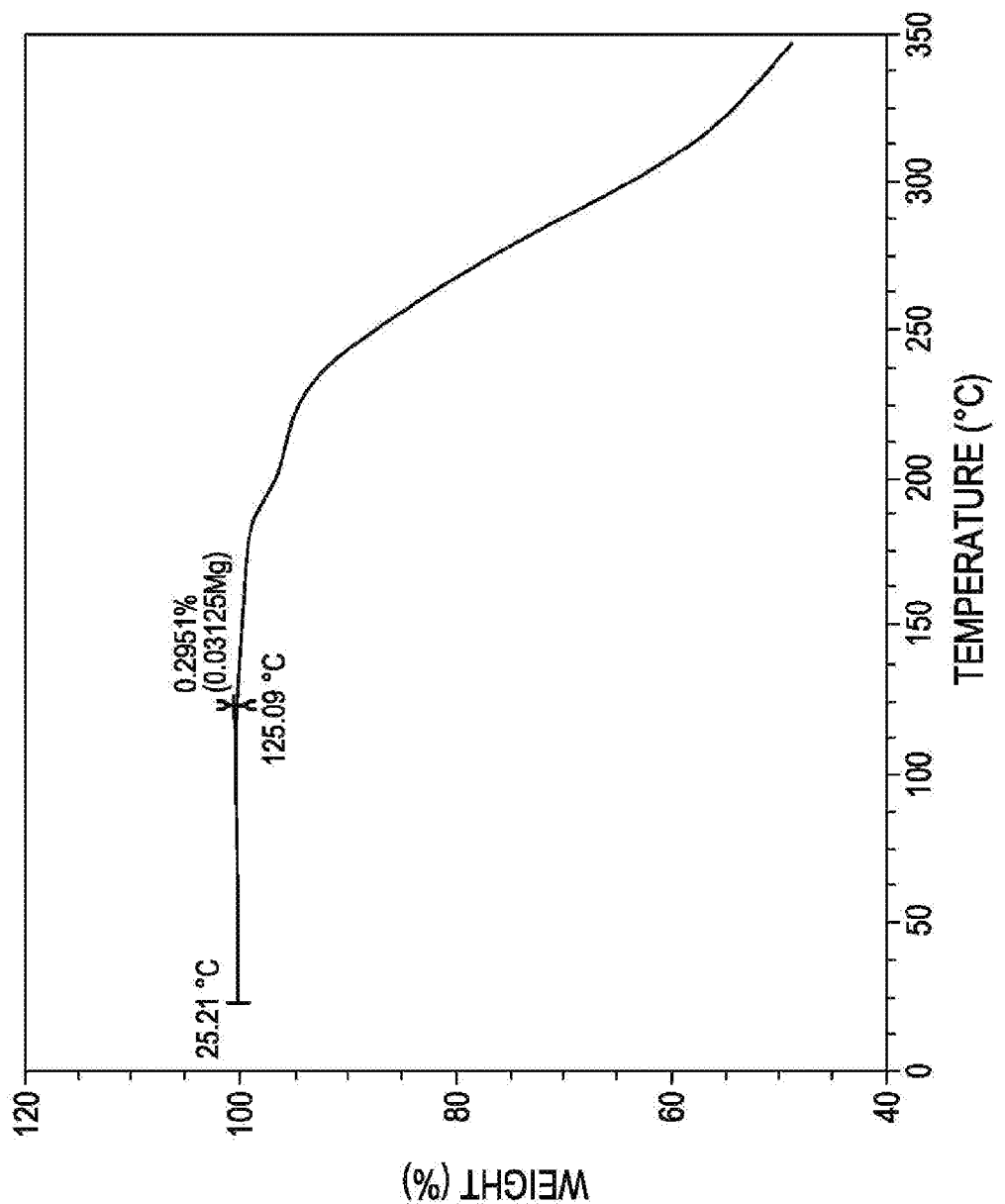
FIG. 3 shows a TG thermogram of crystalline compound 1.
Figure 4:
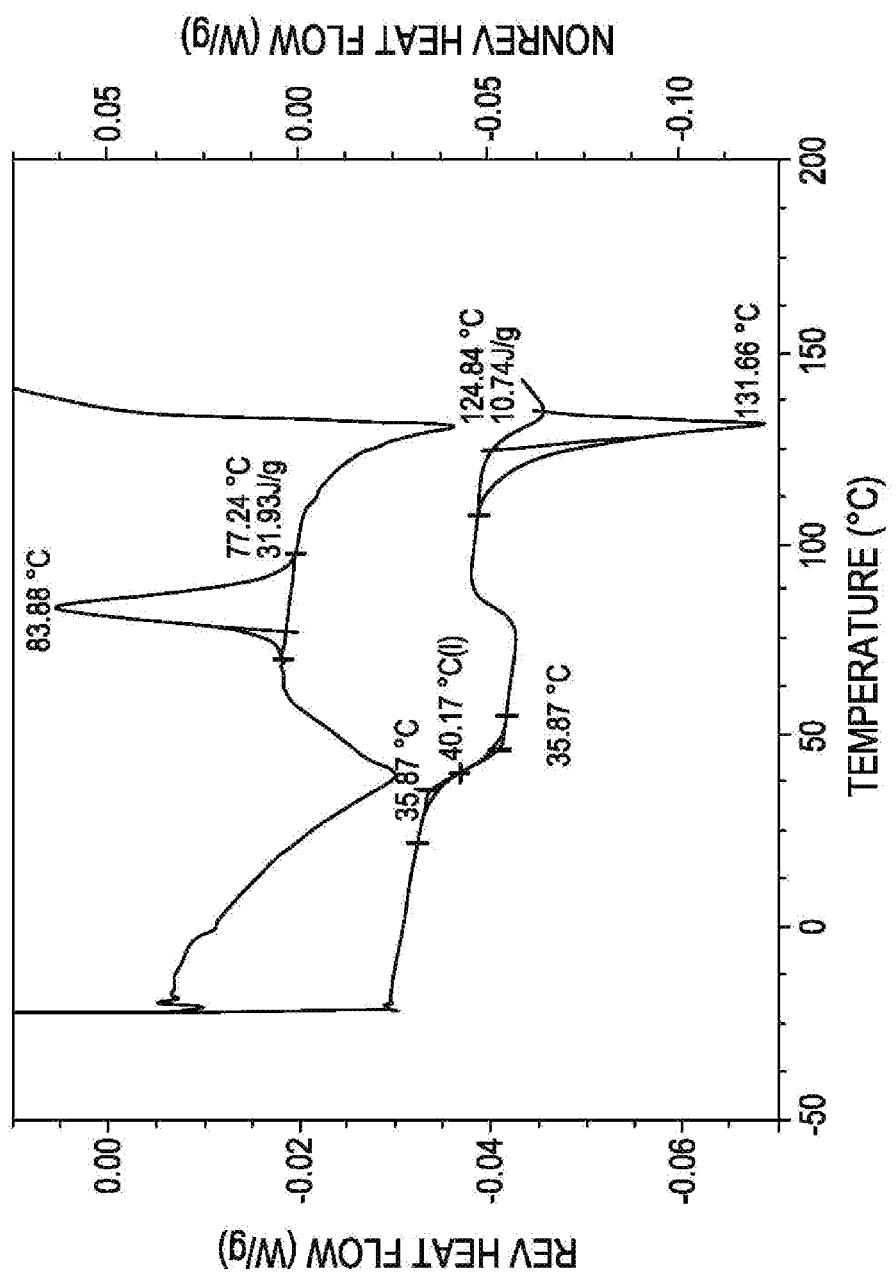
FIG. 4 shows modulated thermograms of amorphous compound 1, reversing heat flow (bottom) and non-reversing heat flow (top).
Figure 5:
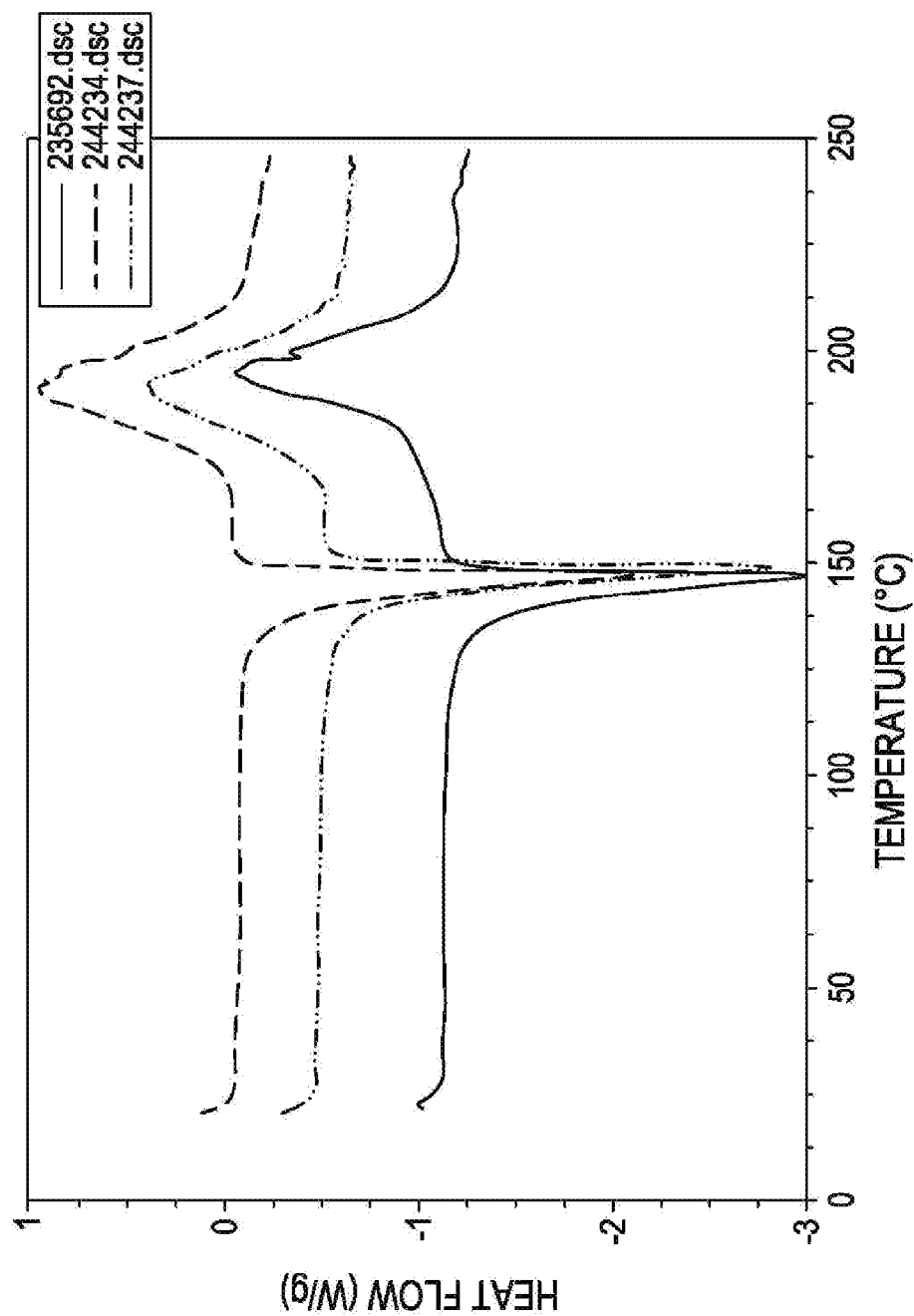
FIG. 5 shows a comparison of DSC thermograms of crystalline compound 1 prepared according to Example 2 (middle), Example 3 (top), and Example 4 (bottom).
Figure 6:
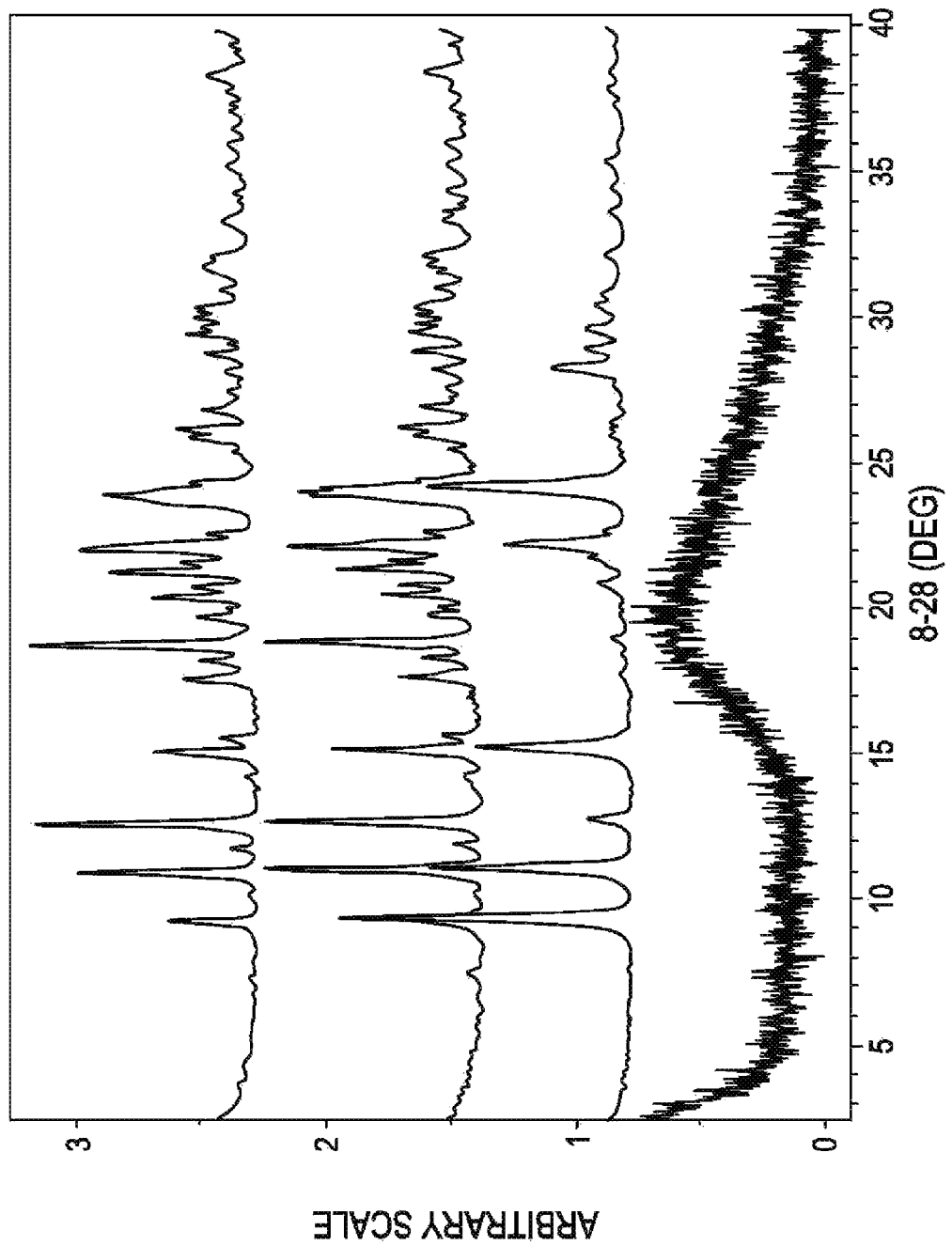
FIG. 6 shows an XRPD pattern of amorphous compound 1 prepared according to Example 1 (bottom), as compared to XRPD patterns of crystalline compound 1 prepared according to Example 2 (top), Example 3 ($2^{nd}$ from bottom), and Example 4 ($2^{nd}$ from top).
Figure 7:
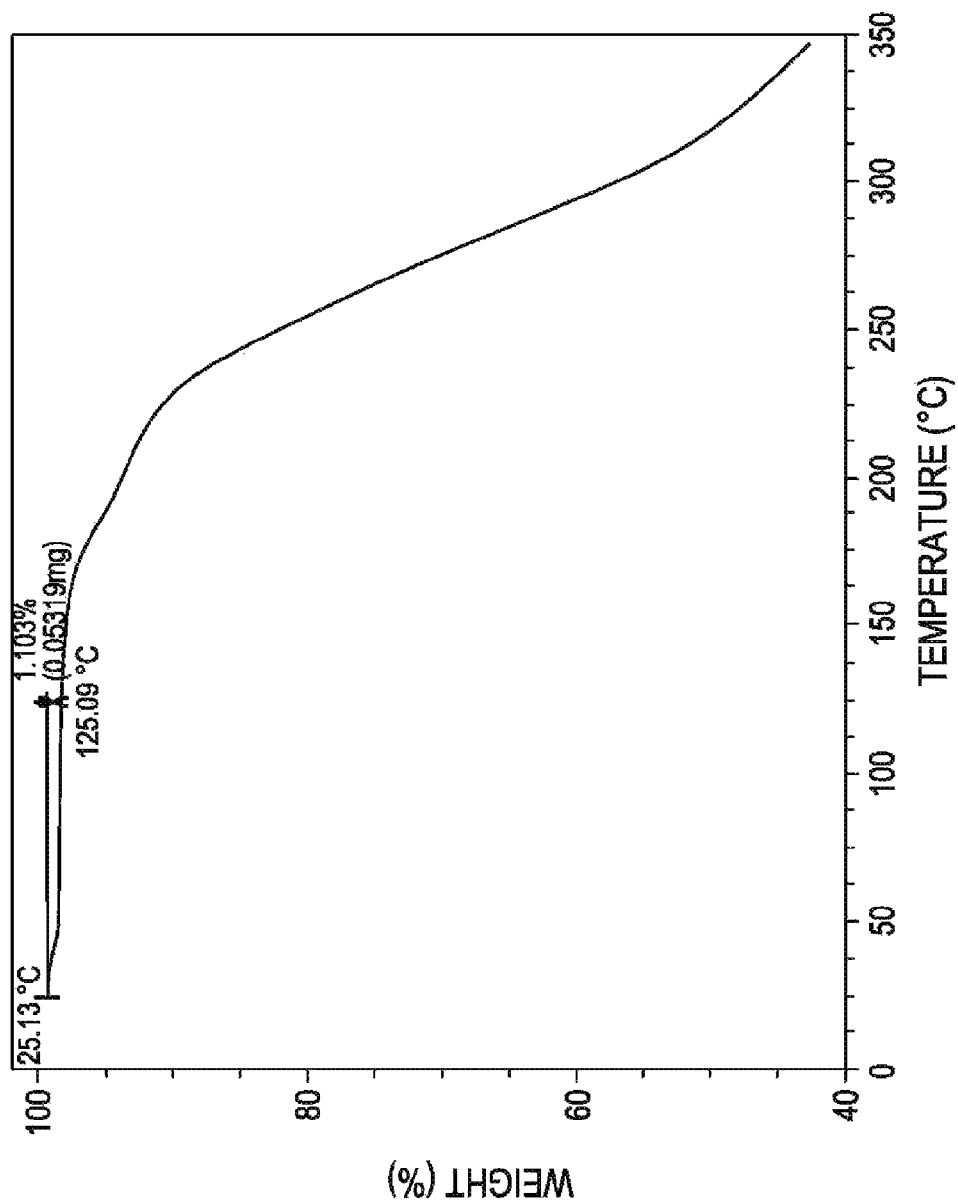
FIG. 7 shows a TG thermogram of amorphous compound 1.

In certain embodiments, the TG thermogram of a crystalline compound of Formula (II) exhibits from 0.0 to 0.3% weight loss in the temperature range of 25 to 125° C. as shown in FIG. 3.

In certain embodiments, a crystalline compound of Formula (II) is not solvated (e.g., the crystal lattice does not comprise molecules of a solvent). In certain alternative embodiments, a crystalline compound of Formula (II) is solvated.

In certain embodiments, the invention relates to a method for the preparation of a crystalline compound of Formula (II),

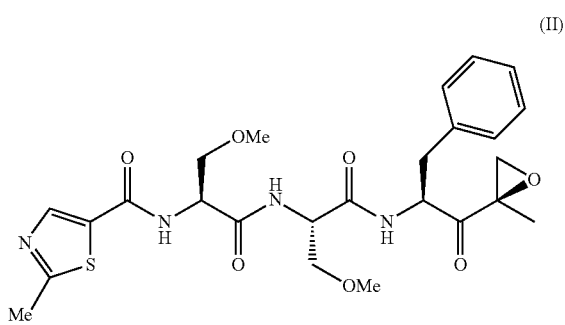 [SMILES: COC[C@H](NC(=O)c1cnc(C)s1)C(=O)N[C@@H](COC)C(=O)N[C@@H](Cc1ccccc1)C(=O)[C@@]1(C)CO1]

comprising (i) reacting a compound of Formula (III)

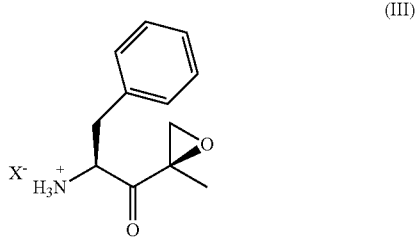

wherein X is any suitable counterion, with a compound of Formula (IV) in an organic solvent

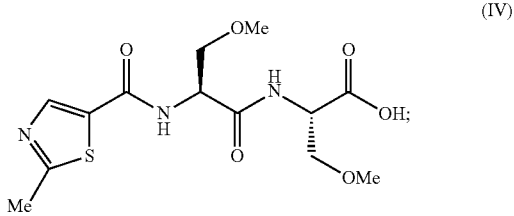 [SMILES: COC[C@H](NC(=O)[C@H](COC)NC(=O)c1cnc(C)s1)C(=O)O]

(ii) preparing a solution of a compound of Formula (II) in the organic solvent; (iii) bringing the solution to supersaturation to permit formation of crystals; and (iv) isolating the crystals to provide a crystalline compound of Formula (II), e.g., by filtering the crystals, by decanting, or by any other suitable separation technique.

In certain embodiments a compound of Formula (II) is not purified by chromatography prior to preparation of the solution in the organic solvent.

In certain embodiments, preparation further comprises inducing crystallization. In certain embodiments, preparation further comprises washing the crystals, e.g., with a solvent or non-solvent fluid. In certain embodiments, preparation further comprises drying, preferably under reduced pressure, such as under vacuum pressure.

In certain embodiments, X is a counterion selected from hydrobromide, hydrochloride, sulfate, phosphate, nitrate, acetate, trifluoroacetate, citrate, methanesulfonate, valerate, oleate, palmitate, stearate, laurate, benzoate, lactate, succinate, tosylate, malonate, maleate, fumarate, succinate, tartrate, mesylate, 2-hydroxyethanesulfonate, and the like. (See, for example, Berge et al. (1977) "Pharmaceutical Salts", J. Pharm. Sci. 66: 1-19.) In certain embodiments, X is selected from trifluoroacetate, methanesulfonate, toluenesulfonate, acetate, chloride, and bromide, preferably trifluoroacetate.

In certain embodiments, the organic solvent is selected from acetonitrile, ethyl acetate, heptanes, hexanes, isopropyl acetate, methanol, methylethyl ketone, tetrahydrofuran, toluene, and water, or any combination thereof. In certain embodiments, the amorphous compound of Formula (II) may be dissolved in an organic solvent selected from acetonitrile, heptanes, hexanes, methanol, tetrahydrofuran, and toluene, or any combination thereof. In certain preferred embodiments, the organic solvent is toluene, tetrahydrofuran, or acetonitrile, preferably acetonitrile or toluene.

In certain embodiments, preparation further comprises washing the crystals of Formula (II). In certain embodiments, washing the crystals comprises washing with a liquid selected from anti-solvent, acetonitrile, heptanes, hexanes, methanol, tetrahydrofuran, toluene, water, or a combination thereof. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene.

In certain embodiments, preparation further comprises drying the crystals of both of Formula (II), preferably under reduced pressure, such as under vacuum pressure.

In certain embodiments, the invention relates to a pharmaceutical composition comprising a crystalline compound of Formula (II) and a pharmaceutically acceptable carrier. In certain embodiments, the pharmaceutical composition is selected from tablets, capsules, and injections.

Uses of Crystalline Tripeptide Epoxy Ketones

Orderly protein degradation is crucial to the maintenance of normal cell functions, and the proteasome is integral to the protein degradation process. The proteasome controls the levels of proteins that are important for cell-cycle progression and apoptosis in normal and malignant cells; for example, cyclins, caspases, BCL2 and nF-kB (Kumatori et al., Proc. Natl. Acad. Sci. USA (1990) 87:7071-7075; Almond et al., Leukemia (2002) 16: 433-443). Thus, it is not surprising that inhibiting proteasome activity can translate into therapies to treat various disease states, such as malignant, non-malignant and autoimmune diseases, depending on the cells involved.

Both in vitro and in vivo models have shown that malignant cells, in general, are susceptible to proteasome inhibition. In fact, proteasome inhibition has already been validated as a therapeutic strategy for the treatment of multiple myeloma. This could be due, in part, to the highly proliferative malignant cell's dependency on the proteasome system to rapidly remove proteins (Rolfe et al., J. Mol. Med. (1997) 75:5-17; Adams, Nature (2004) 4: 349-360). Therefore, certain embodiments of the invention relate to a method of treating a cancer, comprising administering to a subject in need of such treatment an effective amount of a proteasome inhibitor compound disclosed herein. As used herein, the term "cancer" includes, but is not limited to, blood borne and solid tumors. Cancer refers to disease of blood, bone, organs, skin tissue and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute myelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplasmacytic lymphoma (such as Waldenström's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin's lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-entero-pancreatic or gastroenteropancreatic neuroendocrine tumor (GEP-NET), carcinoid, pancreatic endocrine tumor (PET), colorectal adenocarcinoma, colorectal carcinoma, aggressive neuroendocrine tumor, leiomyosarcoma, mucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, thyroid carcinoma, prostate cancer (hormone refractory, androgen independent, androgen dependent, hormone-insensitive), renal cell carcinoma, and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

Many tumors of the haematopoietic and lymphoid tissues are characterized by an increase in cell proliferation, or a particular type of cell. The chronic myeloproliferative diseases (CMPDs) are clonal haematopoietic stem cell disorders characterized by proliferation in the bone marrow of one or more of the myeloid lineages, resulting in increased numbers of granulocytes, red blood cells and/or platelets in the peripheral blood. As such, the use of proteasome inhibitors for the treatment of such diseases is attractive and being examined (Cilloni et al., Haematologica (2007) 92: 1124-1229). CMPD can include chronic myelogenous leukaemia, chronic neutrophilic leukaemia, chronic eosinophilic leukaemia, polycythaemia vera, chronic idiopathic myelofibrosis, essential thrombocythaemia and unclassifiable chronic myeloproliferative disease. An aspect of the invention is the method of treating CMPD comprising administering to a subject in need of such treatment an effective amount of a proteasome inhibitor compound disclosed herein.

Myelodisplastic/myeloproliferative diseases, such as chronic myelomonocytic leukaemia, atypical chronic myeloid leukaemia, juvenile myelomonocytic leukaemia and unclassifiable myelodysplastic/myeloproliferative disease, are characterized by hypercellularity of the bone marrow due to proliferation in one or more of the myeloid lineages. Inhibiting the proteasome with a compound or composition as described herein can serve to treat these myelodysplatic/myeloproliferative diseases by providing a subject in need of such treatment an effective amount of the compound or composition.

Myelodysplastic syndromes (MDS) refer to a group of hematopoietic stem cell disorders characterized by dysplasia and ineffective haematopoiesis in one or more of the major myeloid cell lines. Targeting NF-kB with a proteasome inhibitor in these hematologic malignancies induces apoptosis, thereby killing the malignant cell (Braun et al. Cell Death and Differentiation (2006) 13:748-758). A further embodiment of the invention is a method to treat MDS comprising administering to a subject in need of such treatment an effective amount of a compound disclosed herein. MDS includes refractory anemia, refractory anemia with ringed sideroblasts, refractory cytopenia with multilineage dysplasia, refractory anemia with excess blasts, unclassifiable myelodysplastic syndrome and myelodysplastic syndrome associated with isolated del(5q) chromosome abnormality.

Mastocytosis is a proliferation of mast cells and their subsequent accumulation in one or more organ systems. Mastocytosis includes, but is not limited to, cutaneous mastocytosis, indolent systemic mastocytosis (ISM), systemic mastocytosis with associated clonal haematological non-mast-cell-lineage disease (SM-AHNMD), aggressive systemic mastocytosis (ASM), mast cell leukemia (MCL), mast cell sarcoma (MCS) and extracutaneous mastocytoma. Another embodiment of the invention is a method to treat mastocytosis, comprising administering an effective amount of a compound or composition disclosed herein to a subject diagnosed with mastocytosis.

The proteasome regulates NF-κB, which in turn regulates genes involved in the immune and inflammatory response. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). Thus, in certain embodiments, the invention relates to methods of affecting the level of expression of IL-2, MHC-I, IL-6, TNFα, IFN-β or any of the other previously-mentioned proteins, each method comprising administering to a subject an effective amount of a proteasome inhibitor compound or composition disclosed herein. In certain embodiments, the invention includes a method of treating an autoimmune disease in a mammal comprising administering a therapeutically effective amount of a compound or composition described herein. An "autoimmune disease" herein is a disease or disorder arising from and directed against an individual's own tissues. Examples of autoimmune diseases or disorders include, but are not limited to, inflammatory responses such as inflammatory skin diseases including psoriasis and dermatitis (e.g., atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus or insulin dependent diabetes mellitis); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Beheet disease; giant cell arteritis; immune complex nephritis; IgA nephropathy; IgM polyneuropathies; immune thrombocytopenic purpura (ITP) or autoimmune thrombocytopenia.

The immune system screens for autologous cells that are virally infected, have undergone oncogenic transformation, or present unfamiliar peptides on their surface. Intracellular proteolysis generates small peptides for presentation to T-lymphocytes to induce MHC class I-mediated immune responses. Thus, in certain embodiments, the invention relates to a method of using the compound as an immunomodulatory agent for inhibiting or altering antigen presentation in a cell, comprising exposing the cell (or administering to a subject) to a compound described herein. Specific embodiments include a method of treating graft or transplant-related diseases, such as graft-versus-host disease or host versus-graft disease in a mammal, comprising administering a therapeutically effective amount of a compound described herein. The term "graft" as used herein refers to biological material derived from a donor for transplantation into a recipient. Grafts include such diverse material as, for example, isolated cells such as islet cells; tissue such as the amniotic membrane of a newborn, bone marrow, hematopoietic precursor cells, and ocular tissue, such as corneal tissue; and organs such as skin, heart, liver, spleen, pancreas, thyroid lobe, lung, kidney, tubular organs (e.g., intestine, blood vessels, or esophagus). The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. In some cases, the donor and recipient is the same mammal. Preferably the graft is bone marrow or an organ such as heart and the donor of the graft and the host are matched for HLA class II antigens.

Histiocytic and dendritic cell neoplasms are derived from phagocytes and accessory cells, which have major roles in the processing and presentation of antigens to lymphocytes. Depleting the proteasome content in dendritic cells has been shown to alter their antigen-induced responses (Chapatte et al. Cancer Res. (2006) 66:5461-5468). Thus, another embodiment of the invention comprises administering an effective amount of a compound or composition disclosed herein to a subject with histiocytic or dendritic cell neoplasm. Histiocytic and dendritic cell neoplasms include histiocytic sarcoma, Langerhans cell histiocytosis, Langerhans cell sarcoma, interdigitating dendritic cell sarcoma/tumor, follicular dendritic cell sarcoma/tumor and non-specified dendritic cell sarcoma.

Inhibition of the proteasome has been shown to be beneficial to treat diseases whereby a cell type is proliferating and immune disorders; thus, an embodiment of the invention includes the treatment of lymphoproliferative diseases (LPD) associated with primary immune disorders (PID) comprising administering an effective amount of the disclosed compound to a subject in need thereof. The most common clinical settings of immunodeficiency associated with an increased incidence of lymphoproliferative disorders, including B-cell and T-cell neoplasms and lymphomas, are primary immunodeficiency syndromes and other primary immune disorders, infection with the human immunodeficiency virus (HIV), iatrogenic immunosuppression in patients who have received solid organ or bone marrow allografts, and iatrogenic immunosuppression associated with methotrexate treatment. Other PIDs commonly associated with LPDs, but not limited to, are ataxia telangiectasia (AT), Wiskott-Aldrich syndrome (WAS), common variable immunodeficiency (CVID), severe combined immunodeficiency (SCID), X-linked lymphoproliferative disorder (XLP), Nijmegen breakage syndrome (NBS), hyper-IgM syndrome, and autoimmune lymphoproliferative syndrome (ALPS).

Additional embodiments of the invention relate to methods for affecting the proteasome-dependent regulation of onco-proteins and methods of treating or inhibiting cancer growth, each method comprising exposing a cell (in vivo, e.g., in a subject, or in vitro) to the proteasome inhibitor composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. In certain embodiments, the invention relates to a method for treating p53-related apoptosis, comprising administering to a subject an effective amount of a proteasome inhibitor composition disclosed herein.

Another aspect of the invention relates to the use of proteasome inhibitor compositions disclosed herein for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the β-subunit of human macropain (Kojima, S. et al., *Fed. Eur. Biochem. Soc.*, (1992) 304: 57-60). The APP-processing enzyme cleaves at the $Gln^{15}$-$Lys^{16}$ bond; in the presence of calcium ion, the enzyme also cleaves at the $Met^{-1}$-$Asp^1$ bond and the $Asp^1$-$Ala^2$ bond to release the extracellular domain of β-AP.

One aspect of the invention, therefore, relates to a method of treating Alzheimer's disease, comprising administering to a subject an effective amount of a proteasome inhibitor compound or composition disclosed herein. Such treatment includes reducing the rate of β-AP processing, reducing the rate of β-AP plaque formation, reducing the rate of β-AP generation, and reducing the clinical signs of Alzheimer's disease.

Fibrosis is the excessive and persistent formation of fibrous connective tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activates transcription of target genes upon TGF-β stimulation is regulated by proteasome activity (Xu et al., 2000). However, accelerated degradation of the TGF-β signaling components has been observed in fibrotic conditions, such as cystic fibrosis, injection fibrosis, endomyocardial fibrosis, idiopathic pulmonary fibrosis, myelofibrosis, retroperitoneal fibrosis, progressive massive fibrosis, nephrogenic systemic fibrosis. Other conditions that are often associated with fibrosis include cirrhosis, diffuse parenchymal lung disease, post-vasectomy pain syndrome, tuberculosis, sickle-cell anemia and rheumatoid arthritis. An embodiment of the invention is the method of treating a fibrotic or fibrotic-associated condition comprising administering an effective amount of the composition described herein to a subject in need of such treatment.

The treatment of burn victims is often hampered by fibrosis. Thus, in certain embodiments, the invention relates to the topical or systemic administration of a subject inhibitor to treat burns. Wound closure following surgery is often associated with disfiguring scars, which may be prevented by inhibition of fibrosis. Thus, in certain embodiments, the invention relates to a method for the prevention or reduction of scarring.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., *J. Immun.* (2003) 171: 1515-1525). Therefore, in certain embodiments, the proteasome inhibitor composition may be used for the inhibition of TNFα to prevent and/or treat septic shock.

Ischemia and reperfusion injury results in hypoxia, a condition in which there is a deficiency of oxygen reaching the tissues of the body. This condition causes increased degradation of Iκ-Bα, thereby resulting in the activation of NF-κB (Koong et al., 1994). It has been demonstrated that the severity of injury resulting in hypoxia can be reduced with the administration of a proteasome inhibitor (Gao et al., 2000; Bao et al., 2001; Pye et al., 2003). Therefore, certain embodiments of the invention relate to a method of treating an ischemic condition or reperfusion injury comprising administering to a subject in need of such treatment an effective amount of the proteasome inhibitor compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., *Science*, (1995) 267:960). In certain embodiments, the invention relates to a method for inhibiting or reducing HIV infection in a subject, or a method for decreasing the level of viral gene expression, each method comprising administering to the subject an effective amount of a proteasome inhibitor compound or composition disclosed herein.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, specific proteasome subunits were uniformly up-regulated in hearts of mice which developed chronic myocarditis (Szalay et al, Am J Pathol 168:1542-52, 2006). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronavirus. Yu and Lai (J Virol 79:644-648, 2005) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, likewise requires virally encoded envelop proteins to propagate. Inhibiting the proteasome degradation pathway causes a significant reduction in the amount of secreted envelope proteins (Simsek et al, J Virol 79:12914-12920, 2005). In addition to HBV, other hepatitis viruses (A, C, D and E) may also utilize the ubiquitin-proteasome degradation pathway for secretion, morphogenesis and pathogenesis. Accordingly, in certain embodiments, the invention relates to a method for treating viral infection, such as SARS or hepatitis A, B, C, D and E, comprising contacting a cell with (or administering to a subject) an effective amount of a compound or composition disclosed herein.

In certain embodiments, the disclosed compositions may be useful for the treatment of a parasitic infection, such as infections caused by protozoan parasites. The proteasome of these parasites is considered to be involved primarily in cell differentiation and replication activities (Paugam et al., Trends Parasitol. 2003, 19(2): 55-59). Furthermore, *entamoeba* species have been shown to lose encystation capacity when exposed to proteasome inhibitors (Gonzales, et al., Arch. Med. Res. 1997, 28, Spec No: 139-140). In certain such embodiments, the administrative protocols for the proteasome inhibitor compositions are useful for the treatment of parasitic infections in humans caused by a protozoan parasite selected from *Plasmodium* sps. (including *P. falciparum, P. vivax, P. malariae*, and *P. ovale*, which cause malaria), *Trypanosoma* sps. (including *T. cruzi*, which causes Chagas' disease, and *T. brucei* which causes African sleeping sickness), *Leishmania* sps. (including *L. amazonesis, L. donovani, L. infantum, L. mexicana*, etc.), *Pneumocystis carinii* (a protozoan known to cause pneumonia in AIDS and other immunosuppressed patients), *Toxoplasma gondii, Entamoeba histolytica, Entamoeba invadens*, and *Giardia lamblia*. In certain embodiments, the disclosed proteasome inhibitor compositions are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona*, and *Neurospora crassa*. Other compounds that act as proteasome inhibitors in the treatment of parasitic diseases are described in WO 98/10779, which is incorporated herein in its entirety.

In certain embodiments, the proteasome inhibitor compositions inhibit proteasome activity in a parasite without recovery in red blood cells and white blood cells. In certain such embodiments, the long half-life of blood cells may provide prolonged protection with regard to therapy against recurring exposures to parasites. In certain embodiments, the proteasome inhibitor compositions may provide prolonged protection with regard to chemoprophylaxis against future infection.

Prokaryotes have an equivalent to the eukaryote 20S proteasome particle. Although the subunit composition of the prokaryote 20S particle is simpler than that of eukaryotes, it has the ability to hydrolyze peptide bonds in a similar manner. For example, the nucleophilic attack on the peptide bond occurs through the threonine residue on the N-terminus of the β-subunits. Thus, an embodiment of this invention relates to a method of treating prokaryotic infections, comprising administering to a subject an effective amount of a proteasome inhibitor compound or composition disclosed herein. Prokaryotic infections may include diseases caused by either mycobacteria (such as tuberculosis, leprosy or Buruli ulcer) or archaebacteria.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, a disclosed proteasome inhibitor compound or composition may be useful in the treatment and/or prevention of diseases associated with bone loss, such as osteoporosis.

Thus, in certain embodiments, the invention relates to a method for treating a disease or condition selected from cancer, autoimmune disease, graft or transplant-related condition, neurodegenerative disease, fibrotic-associated condition, ischemic-related conditions, infection (viral, parasitic or prokaryotic) and diseases associated with bone loss, comprising administering a compound or composition as disclosed herein.

Administration of Crystalline Tripeptide Epoxy Ketones

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10)

glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient may be mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like. In certain embodiments the crystalline tripeptide epoxyketone is administered to a mammal as a capsule. In another embodiment, the crystalline tripeptide epoxyketone is a compound of formula (I). In a more preferred embodiment, the crystalline tripeptide epoxyketone is a compound of formula (II).

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microcapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These inhibitors(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

Definitions

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$alkoxyalkyl" refers to a $C_{1-6}$alkyl group substituted with an alkoxy group, thereby forming an ether.

The term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

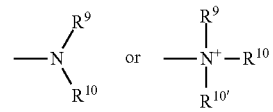

wherein $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, the amino group is basic, meaning the protonated form has a $pK_a \geq 7.00$.

The terms "amide" and "amido" are art-recognized as an amino-substituted carbonyl and includes a moiety that can be represented by the general formula:

wherein $R^9$, $R^{10}$ are as defined above. Preferred embodiments of the amide will not include imides which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formula:

wherein X is a bond or represents an oxygen or a sulfur, and $R^{11}$ represents a hydrogen, an alkyl, an alkenyl, —$(CH_2)_m$—

$R^8$ or a pharmaceutically acceptable salt, $R^{11'}$ represents a hydrogen, an alkyl, an alkenyl or —$(CH_2)_m$—$R^8$, where m and $R^8$ are as defined above. Where X is an oxygen and $R^{11}$ or $R^{11'}$ is not hydrogen, the formula represents an "ester". Where X is an oxygen, and $R^{11}$ is a hydrogen, the formula represents a "carboxylic acid".

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, isoxazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, tetrahydrofuran, piperidine, piperazine, pyrrolidine, morpholine, lactones, lactams, and the like.

The term "$C_{1-6}$heterocycloalkyl", as used herein, refers to a $C_{1-6}$alkyl group substituted with a heterocyclyl group.

The term "$C_{1-6}$hydroxyalkyl" refers to a $C_{1-6}$alkyl group substituted with a hydroxy group.

As used herein, the term "inhibitor" is meant to describe a compound that blocks or reduces an activity of an enzyme (for example, inhibition of proteolytic cleavage of standard fluorogenic peptide substrates such as suc-LLVY-AMC, Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

As used herein, the term "orally bioavailable" is meant to describe a compound administered to a mouse at 40 mg/kg or less, 20 mg/kg or less, or even 10 mg/kg or less, wherein one hour after oral administration such a compound shows at least about 50%, at least about 75% or even at least about 90% inhibition of proteasome CT-L activity in the blood.

As used herein, the term "peptide" includes not only standard amide linkage with standard α-substituents, but commonly utilized peptidomimetics, other modified linkages, non-naturally occurring side chains, and side chain modifications, as detailed below.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "proteasome" as used herein is meant to include immuno- and constitutive proteasomes.

The term "substantially pure" as used herein, refers to a crystalline polymorph that is greater than 90% pure, meaning that contains less than 10% of any other compound, including the corresponding amorphous compound. Preferably, the crystalline polymorph is greater than 95% pure, or even greater than 98% pure.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "proteasome" as used herein is meant to include immuno- and constitutive proteasomes.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxy-carbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "thioether" refers to an alkyl group, as defined above, having a sulfur moiety attached thereto. In preferred embodiments, the "thioether" is represented by —S-alkyl. Representative thioether groups include methylthio, ethylthio, and the like.

As used herein, the term "treating" or "treatment" includes reversing, reducing, or arresting the symptoms, clinical signs, and underlying pathology of a condition in manner to improve or stabilize a subject's condition.

EXEMPLIFICATION

Example 1

Synthesis of Compound 1

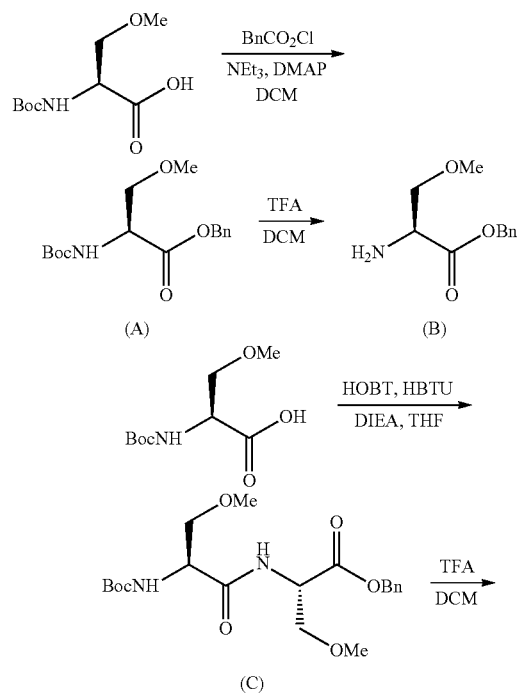

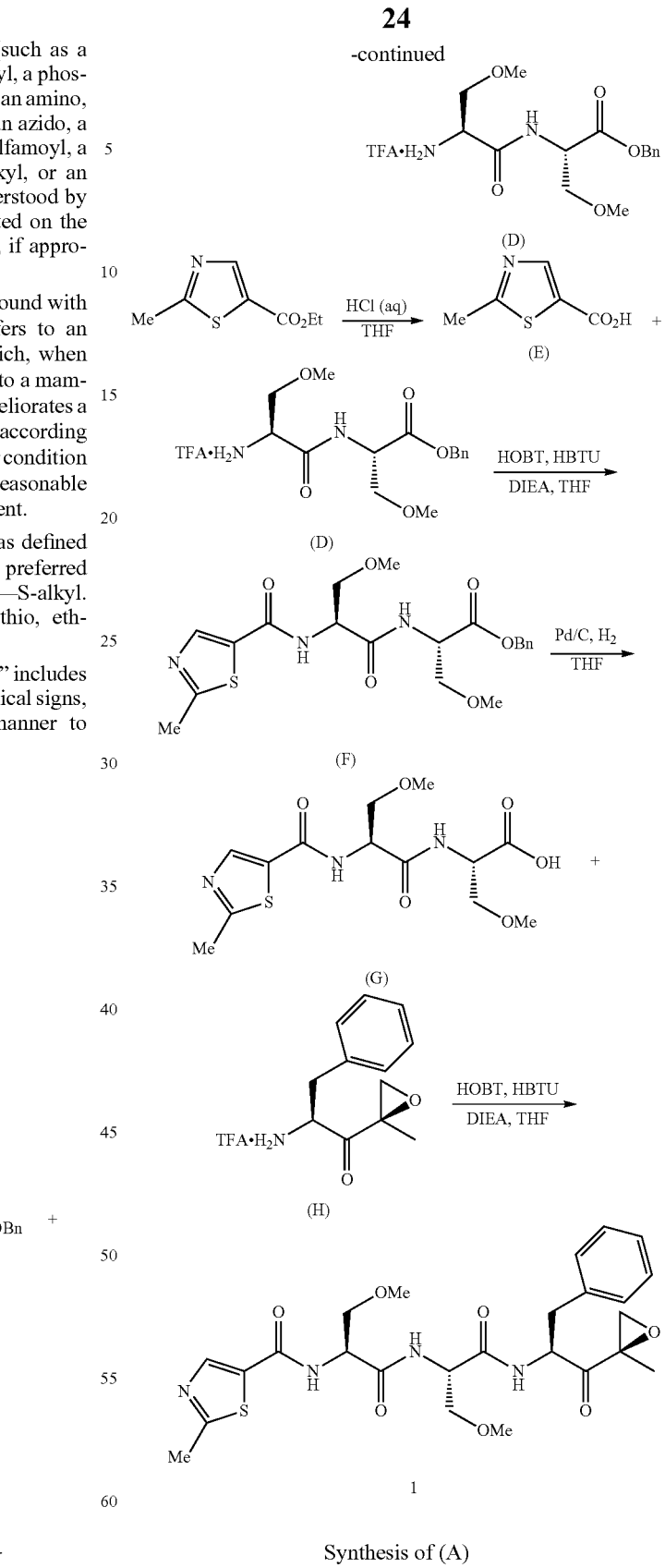

Synthesis of (A)

To a 0° C. solution of N-Boc serine(methyl ether) (43.8 g, 200 mmol), triethylamine (26.5 g, 260 mmol) and 4-(dimethylamino)pyridine in dichloromethane (1.2 L) was added a solution of benzyl chloroformate (41 g, 240 mmol) in dichloromethane (250 mL) over 30 minutes. The resulting mixture was stirred at the same temperature for another 3 hours. Saturated aqueous sodium bicarbonate (200 mL) was added and organic layer was separated, the residual mixture was extracted with dichloromethane (2×400 mL). The combined organic layers were washed with saturated aqueous sodium bicarbonate (200 mL) and brine (200 mL), dried over sodium sulfate and filtered through Celite-545. The solvents were removed under reduced pressure and residue was purified by flash chromatography (silica gel, hexane and ethyl acetate). Compound (A) (54 g) was isolated and characterized by LC/MS (LRMS (MH) m/z: 310.16).

Synthesis of (B)

To a 0° C. solution of Compound (A) (54 g) in dichloromethane (200 mL) was added trifluoroacetic acid (200 mL) over 10 minutes, and the resulting mixture was stirred at the same temperature for another 3 hours. The solvents were removed under reduced pressure and the residue was placed under high vacuum overnight giving the TFA salt of Compound (B), which was characterized by LC/MS (LRMS (MH) m/z: 210.11).

Synthesis of (C)

To a 0° C. solution of Compound (B) (43.8 g, 200 mmol), N-Boc serine(methyl ether) (36.7 g, 167 mmol), HOBT (27 g, 200 mmol) and HBTU (71.4 g, 200 mmol) in tetrahydrofuran (1.2 L) was added a solution of N,N-diethylisopropylamine (75 g, 600 mmol) in tetrahydrofuran (250 mL) over 10 minutes, and the pH of the resulting mixture was ~8. The mixture was stirred at room temperature for another 5 hours. Most of the solvent were removed under reduced pressure at room temperature and diluted with saturated aqueous sodium bicarbonate (400 mL). Then it was extracted with ethyl acetate (3×400 mL), washed with sodium bicarbonate (100 mL) and brine (100 mL). The combined organic layers were dried over sodium sulfate and filtered through Celite-545. The solvents were removed under reduced pressure and residue was purified by flash chromatography (silica gel, hexane and ethyl acetate). Compound (C) (65 g) was isolated and characterized by LC/MS (LRMS (MH) m/z: 411.21).

Synthesis of (D)

To a 0° C. solution of Compound (C) (18 g) in dichloromethane (100 mL) was added trifluoroacetic acid (80 mL) over 5 minutes, and the resulting mixture was stirred at the same temperature for another 3 hours. The solvents were removed under reduced pressure and the residue was placed under high vacuum overnight giving the TFA salt of intermediate (D), which was characterized by LC/MS (LRMS (MH) m/z: 311.15).

Synthesis of (E)

To a 0° C. solution of ethyl 2-methyl-thiazole-5-carboxylate (15 g, 88 mmol) in tetrahydrofuran (50 mL) was added aqueous sodium hydroxide solution (5 N, 50 mL) over 10 minutes, and the resulting solution was stirred at room temperature for another 2 hours. It was then acidified with hydrochloric acid (2 N) to pH=1 and extracted with tetrahydrofuran (3×100 mL). The combined organic layers were washed with brine (30 mL) and dried over sodium sulfate. Most of the solvents were removed under reduced pressure and the residue was lyophilized to afford Compound (E) (14 g).

Synthesis of (F)

To a 0° C. solution of Compound (D) (41 mmol) and 2-methyl-thiazole-5-carboxylic acid (E) (6.0 g, 42 mmol), HOBT (7.9 g, 50 mmol) and HBTU (18.0 g, 50 mmol) in tetrahydrofuran (800 mL) was added a solution of N,N-diethylisopropylamine (~50 g) in tetrahydrofuran (200 mL) over 5 minutes until its pH reached approximately 8.5. The resulting mixture was stirred at same temperature overnight. It was then quenched with saturated aqueous sodium bicarbonate solution (200 mL), and most of the solvents were removed under reduced pressure. The residual mixture was extracted with ethyl acetate (3×400 mL). The combined organic layers were washed with saturated aqueous sodium bicarbonate (200 mL) and brine (100 mL), dried over sodium sulfate and filtered through Celite-545. The solvents were removed under reduced pressure and residue was purified by flash chromatography (silica gel, ethyl acetate with 2% methanol). Compound (F) (17.1 g) was isolated and characterized by LC/MS (LRMS (MH) m/z: 436.15).

Synthesis of (G)

To a solution of Compound (F) (17.1 g, 95 mmol) in methanol (300 mL) was added 10% Pd/C (3 g). The resulting mixture was allowed to stir under 1 atmosphere of hydrogen for 48 hours. The mixture was filtered through Celite 545 and the filter cake was washed with methanol (~200 mL). The organic layers were concentrated under reduced pressure and placed under high vacuum to yield Compound (G), which was characterized by LC/MS (LRMS (MH) m/z: 346.1).

Synthesis of (H)

N-Boc phenylalanine-ketoepoxide (140 mg, 0.46 mmol) was diluted with DCM (2 mL) and cooled to 0° C. To this solution was added trifluoroacetic acid (6 mL). The cooling bath was removed and the reaction stirred for 1 hour at which time TLC showed complete consumption of starting material. The resulting solution was concentrated under reduced pressure and placed under high vacuum to yield TFA salt of Compound (H).

Synthesis of Compound 1

To a 0° C. solution of aforementioned Compounds (H) (131 mg, 0.38 mmol) and (J) (0.46 mmol), HOBT (75 mg, 0.48 mmol) and HBTU (171 mg, 0.48 mmol) in tetrahydrofuran (20 mL) and N,N-dimethylformamide (10 mL) was added N,N-diethylisopropylamine (1 mL) dropwise. The mixture was stirred at the same temperature for another 5 hours. It was then quenched with saturated aqueous sodium bicarbonate solution (20 mL), and most of the solvents were removed under reduced pressure. The residual mixture was then extracted with ethyl acetate (3×40 mL). The combined organic layers were washed with saturated aqueous sodium bicarbonate (20 mL) and brine (10 mL), dried over sodium sulfate and filtered through Celite-545. The solvents were removed under reduced pressure and residue was purified by HPLC (0.02 M aqueous ammonium acetate and acetonitrile (66/34) to afford Compound 1 (92 mg), which was lyophilized and characterized by LC/MS (LRMS (MH) m/z: 533.2).

Example 2

Amorphous Compound 1 (50 mg) was dissolved in acetonitrile (1 mL), then deionized water (2 mL) was added, and the solution brought to supersaturation by slowly evaporating off 1 mL over about 1-2 weeks. The resulting crystals were filtered, washed with 1 mL 1:2 acetonitrile-water, and dried under vacuum for 12 hours to provide a crystalline polymorph of Compound 1 (25 mg) with a melting point of 148° C. The characteristic DSC curve of the sample is shown in FIG. 1 as recorded on a TA Instruments Differential Scanning calorimeter 2920 at a heating rate of 10° C./minute.

Example 3

Amorphous Compound 1 (611 mg) was dissolved in tetrahydrofuran (5 mL), followed by addition of hexanes (5 mL) and the solution was seeded with crystalline polymorph Compound 1 as prepared in Example 2, and the solution brought to supersaturation by slowly evaporating off 5 mL over about 17 hours. The resulting crystals were filtered, washed with 1 mL 1:1 tetrahydrofuran-hexanes, and dried under vacuum for 12 hours to provide a crystalline polymorph of Compound 1 (150 mg) with a melting point of 147° C.

Example 4

Amorphous Compound 1 (176 mg) was dissolved in tetrahydrofuran (5 mL), then toluene (25 mL) was added. The solution was seeded with crystalline polymorph Compound 1 as prepared in Example 2, and the solution was brought to supersaturation by slowly evaporating off 20 mL over about 2 days. The resulting crystals were filtered, washed with 15 mL toluene, and dried under vacuum for 12 hours to provide a crystalline polymorph of Compound 1 (88 mg) with a melting point of 149° C.

Example 5

Amorphous Compound 1 (312 mg) was dissolved in toluene (50 mL), heated to about 100° C. to complete dissolution, then hexanes (50 mL) were added and the solution was seeded with crystalline polymorph Compound 1 as prepared in Example 2, and the solution brought to supersaturation by slowly evaporating off 60 mL over about 2 days. The resulting crystals were filtered, washed with 10 mL toluene, and dried under vacuum for 12 hours to provide a crystalline polymorph of Compound 1 (156 mg) with a melting point of 149° C.

Example 6

Amorphous Compound 1 (1.4 g) was dissolved in toluene (25 mL), heated to about 50° C. to complete dissolution, then brought to supersaturation by cooling to 22° C. and allowing the compound to crystallize for 12 hours. The resulting crystals were filtered, washed with 5 mL hexanes, and dried under vacuum for 12 hours to provide a crystalline polymorph of Compound 1 (0.94 g) with a melting point of 149° C.

Example 7

Synthesis of Compound 1

Synthesis of (H)

N-Boc phenylalanine-ketoepoxide (1.0 equivalent) was dissolved in DCM (3 L/kg of N-Boc phenylalanine-ketoepoxide) in a 3-neck round bottom flask under inert atmosphere and the solution was cooled in ice bath. Then, TFA (5.0 equivalents) was added at a rate to maintain the internal temperature below 10° C. The reaction mixture was then warmed to approximately 20° C. and stirred for 1 to 3 hours. MTBE (3.6 L/kg of N-Boc phenylalanine-ketoepoxide) was then added to the reaction mixture while maintaining mixture temperature below 25° C. Heptane (26.4 L/kg of N-Boc phenylalanine-ketoepoxide) was then added the reaction was cooled to between −5 and 0° C. for 2 to 3 hours to allow crystallization of Compound (H). The white solid was filtered and rinsed with heptane (3 L/kg of N-Boc phenylalanine-ketoepoxide). The white solid was then under vacuum for 12 hours at 22° C. Yield obtained was 86%, with HPLC purity 99.4%.

Synthesis of Compound 1

Compound (H) (1.2 equivalents), Compound (G) (1.0 equivalent), HBTU (1.2 equivalents), HOBT (1.2 equivalents) and N-methylpyrrolidinone (8 L/kg of Compound (G)) were added to a dry flask under inert atmosphere, and the mixture was stirred at 23° C. to complete dissolution. The reaction was then cooled to between −5 and 0° C., and diisopropylethylamine (2.1 equivalents) was added over 15 minutes, while maintaining an internal reaction temperature of less than 0° C. The reaction mixture was stirred at 0° C. for 12 hours.

Crude Compound 1 was precipitated by pouring the reaction mixture onto 8% sodium bicarbonate (40 L/kg of Compound (G)) and the suspension of crude Compound 1 was stirred for 12 hours at 20 to 25° C., followed by stirring at 0 to 5° C. for 1 hour. The white solid was filtered and rinsed with water (5 L/kg of Compound (G)). The white solid was then reslurried in water (15 L/kg) for 3 hours at 20 to 25° C., filtered and rinsed with water (5 L/kg of Compound (G)) and isopropyl acetate (2×2 L/kg of Compound (G)). The white solid was dried under vacuum at 45° C. to constant weight. Yield of crude Compound 1 was 65%, with HPLC purity of 97.2%.

Crude Compound 1 was completely dissolved in isopropyl acetate (20 L/kg of crude Compound 1) by stirring and heating at 85° C. The solution was then hot filtered to remove any particulate mater and the solution was re-heated to 85° C. to provide clear solution. The clear solution was allowed to cool at 10° C. per hour to 65° C. before adding seed crystals. The solution was allowed to cool at 10° C. per hour to 20° C., when substantial crystallization of Compound 1 occurred. The suspension was stirred at 20° C. for 6 hours, followed by stirring at 0 to 5° C. for a minimum of 2 hours and filtration and rinsing with isopropyl acetate (1 L/kg of crude Compound 1). The purified Compound 1 was dried under vacuum at 45° C. for a minimum of 24 hours to constant weight. Yield of Compound 1 was 87%, with HPLC purity 97.2%.

Example 8

Synthesis of Compound 1

Compound (H) (1.1 equivalents), Compound (G) (1.0 equivalent), HBTU (1.5 equivalents), HOBT (1.5 equivalents) and DMF (8 L/kg of Compound (G)) were added to a dry flask under inert atmosphere, and the mixture was stirred at 23° C. to complete dissolution. The reaction was then cooled to between −5 and 0° C., and diisopropylethylamine (2.1 equivalents) was added over 15 minutes, while maintaining an internal reaction temperature of less than 0° C. The reaction mixture was then stirred at 0° C. for 3 hours.

The reaction mixture was quenched by addition of prechilled saturated sodium bicarbonate (94 L/kg of Compound (G)), while maintaining internal temperature of less 10° C. The content was then transferred to a separatory funnel. The mixture was extracted with ethyl acetate (24 L/kg of Compound (G)), and the organic layer was washed with saturated sodium bicarbonate (12 L/kg of Compound (G)) and with saturated sodium chloride (12 L/kg of Compound (G).

The organic layer was concentrated under reduced pressure with a bath temperature of less than 30° C. to 15 L/kg of Compound (G), followed by co-distillation with isopropyl acetate (2×24 L/kg of PR-022). Final volume was adjusted to 82 L/kg of Compound (G) with isopropyl acetate before heating to 60° C. to obtain a clear solution. The clear solution mixture was allowed to cool to 50° C. before adding seed crystals. The solution was allowed to cool to 20° C., when substantial crystallization of Compound 1 had occurred. The suspension was stirred at 0° C. for 12 hours before filtration and rinsing with isopropyl acetate (2 L/kg of Compound 1). Compound 1 was dried under vacuum at 20° C. for 12 hours to constant weight. Yield of Compound 1 was 48%, with HPLC purity of 97.4%.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

We claim:

1. A pharmaceutical composition comprising a pharmaceutically acceptable carrier and a crystalline compound of Formula (II)

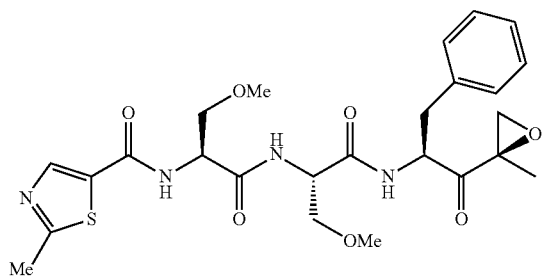

wherein the crystalline compound has an X-ray powder diffraction pattern comprising a characteristic peak expressed in degrees 2θ at 8.94; 9.39; 9.76; 10.60; 11.09; 12.74; 15.27; 17.74; 18.96; 20.58; 20.88; 21.58; 21.78; 22.25; 22.80; 24.25; 24.66; 26.04; 26.44; 28.32; 28.96; 29.65; 30.22; 30.46; 30.78; 32.17; 33.65; 34.49; 35.08; 35.33; 37.85; and 38.48; and the crystalline compound has a melting point of about 140° C. to about 155° C.

2. The pharmaceutical composition of claim 1, wherein the melting point is about 145° C. to about 150° C.

3. The pharmaceutical composition of claim 1, wherein the composition is a parenterally administrable composition.

4. The pharmaceutical composition of claim 1, wherein the composition is an orally administrable composition.

5. The pharmaceutical composition of claim 4, wherein the orally administrable composition is selected from the group consisting of a tablet, a capsule, a granule, a powder and a syrup.

6. The pharmaceutical composition of claim 4, wherein the orally administrable composition is a tablet.

7. The pharmaceutical composition of claim 4, wherein the orally administrable composition is a capsule.

8. The pharmaceutical composition of claim 4, wherein the orally administrable composition is a granule.

9. The pharmaceutical composition of claim 4, wherein the orally administrable composition is a powder.

10. The pharmaceutical composition of claim 3, wherein the crystalline compound exhibits a differential scanning calorimetry (DSC) thermogram characterized with an endothermic peak at 147° C.

11. The pharmaceutical composition of claim 3, wherein the crystalline compound exhibits from 0.0 to 0.3% weight loss in the temperature range of 25° C. to 125° C. in a thermogravimetric analysis.

* * * * *